(12) United States Patent
Naples et al.

(10) Patent No.: US 12,023,464 B2
(45) Date of Patent: Jul. 2, 2024

(54) CASSETTE FOR RETENTION OF FLUID PATH COMPONENTS FOR FLUID INJECTOR SYSTEM

(71) Applicant: Bayer HealthCare LLC, Whippany, NJ (US)

(72) Inventors: Andrew Naples, Mars, PA (US); Kevin Cowan, Allison Park, PA (US); Michael Spohn, Fenelton, PA (US); John Haury, Sewickley, PA (US); Patrick Campbell, Apollo, PA (US); James Dedig, Pittsburgh, PA (US); Randy Lee, Pittsburgh, PA (US); John Caswell, Nashua, NH (US); Katherine MacNamee, Litchfield, NH (US); James Tirone, Hollis, NH (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 18/254,586

(22) PCT Filed: Nov. 30, 2021

(86) PCT No.: PCT/US2021/061201
§ 371 (c)(1),
(2) Date: May 25, 2023

(87) PCT Pub. No.: WO2022/119837
PCT Pub. Date: Jun. 9, 2022

(65) Prior Publication Data
US 2024/0017003 A1 Jan. 18, 2024

Related U.S. Application Data

(60) Provisional application No. 63/199,010, filed on Dec. 1, 2020.

(51) Int. Cl.
*A61M 5/145* (2006.01)
*A61M 5/168* (2006.01)
*A61M 5/36* (2006.01)

(52) U.S. Cl.
CPC .... *A61M 5/14546* (2013.01); *A61M 5/16881* (2013.01); *A61M 5/365* (2013.01)

(58) Field of Classification Search
CPC .......... A61M 5/14546; A61M 5/16881; A61M 5/365; A61M 5/14; A61M 5/142;
(Continued)

(56) References Cited

U.S. PATENT DOCUMENTS

| 352,715 A | 11/1886 | Sandmark |
| 508,584 A | 11/1893 | Stevens |

(Continued)

FOREIGN PATENT DOCUMENTS

| CN | 103917269 A | 7/2014 |
| CN | 105521533 A | 4/2016 |

(Continued)

OTHER PUBLICATIONS

PCT Application No. PCT/US2023/025159 entitled "Disinfecting Cap For Fluid Path Element", filed Jun. 13, 2023.

(Continued)

*Primary Examiner* — Jason E Flick
(74) *Attorney, Agent, or Firm* — Joseph L. Kent; James R. Stevenson; David Schramm

(57) ABSTRACT

A cassette for holding fluid path components for a fluid injector may include a body defining at least one feature for holding at least one fluid path component for the fluid injector; and a connecting member for removably connecting the body of the cassette to the fluid injector, the connecting member operatively connected to the body, wherein the connecting member comprises at least one pivotable (Continued)

connecting feature protruding from the body, and wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body of the cassette is positioned for operative connection to a corresponding feature of the fluid injector.

24 Claims, 17 Drawing Sheets

(58) Field of Classification Search
CPC ...... A61M 2205/3334; A61M 2205/60; A61M 2205/6072; A61M 2205/12; A61M 5/36; A61M 2005/1402; A61M 5/1413; A61M 5/16877; A61M 5/168
See application file for complete search history.

(56) References Cited

U.S. PATENT DOCUMENTS

| | | |
|---|---|---|
| 798,093 A | 8/1905 | Edward |
| 817,054 A | 4/1906 | Daniel |
| 937,029 A | 10/1909 | Blessing et al. |
| 945,143 A | 1/1910 | Iacques |
| 1,388,946 A | 8/1921 | Goold |
| 1,930,929 A | 10/1933 | Joel et al. |
| 2,062,285 A | 12/1936 | Sam et al. |
| 2,511,291 A | 6/1950 | Mueller |
| 2,514,575 A | 7/1950 | Hein et al. |
| 2,583,206 A | 1/1952 | Borck et al. |
| 2,592,381 A | 4/1952 | Blackman |
| 2,616,422 A | 11/1952 | Jones |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Awshe et al. |
| 2,911,972 A | 11/1959 | Elinger |
| 2,915,986 A | 12/1959 | Sisson |
| 2,935,067 A | 5/1960 | Bouet |
| 2,950,717 A | 8/1960 | Bonet |
| 3,101,712 A | 8/1963 | Strazdins et al. |
| 3,155,281 A | 11/1964 | Stracey |
| 3,159,312 A | 12/1964 | Van Sciver, II |
| 3,161,194 A | 12/1964 | Chapman |
| 3,161,195 A | 12/1964 | Taylor et al. |
| 3,166,070 A | 1/1965 | Everett |
| 3,172,577 A | 3/1965 | Hartung |
| 3,190,619 A | 6/1965 | Penney et al. |
| 3,199,511 A | 8/1965 | Kulick |
| 3,231,139 A | 1/1966 | Bouet |
| 3,276,472 A | 10/1966 | Jinkens et al. |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,412,906 A | 11/1968 | Dinger |
| 3,442,424 A | 5/1969 | Sam et al. |
| 3,471,058 A | 10/1969 | Peter et al. |
| 3,473,524 A | 10/1969 | John |
| 3,474,844 A | 10/1969 | Rudolph et al. |
| 3,506,163 A | 4/1970 | James et al. |
| 3,507,278 A | 4/1970 | Winfried |
| 3,527,215 A | 9/1970 | Harry |
| 3,557,788 A | 1/1971 | Swartz |
| 3,613,963 A | 10/1971 | Berkmuller |
| 3,618,846 A | 11/1971 | Poli |
| 3,635,444 A | 1/1972 | Potter |
| 3,671,208 A | 6/1972 | Wayne |
| 3,699,961 A | 10/1972 | Szpur |
| 3,719,207 A | 3/1973 | Takeda |
| 3,736,932 A | 6/1973 | Satchell |
| 3,785,367 A | 1/1974 | Fortin et al. |
| 3,826,409 A | 7/1974 | Chilcoate |
| 3,868,967 A | 3/1975 | Harding |
| 3,873,003 A | 3/1975 | Seiferth et al. |
| 3,938,514 A | 2/1976 | Boucher |
| 3,998,223 A | 12/1976 | Dawe |
| 4,035,461 A | 7/1977 | Korth |
| 4,041,944 A | 8/1977 | Rhodes |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,140,117 A | 2/1979 | Buckles et al. |
| 4,171,698 A | 10/1979 | Genese |
| 4,204,775 A | 5/1980 | Speer |
| 4,208,136 A | 6/1980 | King et al. |
| 4,236,516 A | 12/1980 | Nilson |
| 4,245,655 A | 1/1981 | Patel |
| 4,312,344 A | 1/1982 | Nilson |
| 4,318,400 A | 3/1982 | Peery et al. |
| 4,325,369 A | 4/1982 | Nilson |
| 4,329,067 A | 5/1982 | Goudy, Jr. |
| 4,349,129 A | 9/1982 | Amneus |
| 4,392,491 A | 7/1983 | Takasugi et al. |
| 4,411,656 A | 10/1983 | Cornett |
| 4,419,096 A | 12/1983 | Leeper et al. |
| 4,438,845 A | 3/1984 | Mochow |
| 4,441,823 A | 4/1984 | Power et al. |
| 4,444,310 A | 4/1984 | Odell |
| 4,526,296 A | 7/1985 | Berger et al. |
| 4,610,665 A | 9/1986 | Matsumoto et al. |
| 4,741,733 A | 5/1988 | Winchell et al. |
| 4,747,839 A | 5/1988 | Tarello et al. |
| 4,753,638 A | 6/1988 | Peters |
| 4,773,458 A | 9/1988 | Touzani |
| 4,824,145 A | 4/1989 | Carlsson |
| 4,850,807 A | 7/1989 | Frantz |
| 4,895,570 A | 1/1990 | Larkin |
| 4,904,239 A | 2/1990 | Winchell et al. |
| 4,952,068 A | 8/1990 | Flint |
| 4,969,879 A | 11/1990 | Lichte |
| 5,000,739 A | 3/1991 | Kulisz et al. |
| 5,011,477 A | 4/1991 | Winchell et al. |
| 5,026,348 A | 6/1991 | Venegas |
| 5,033,631 A | 7/1991 | Nightingale |
| 5,048,684 A | 9/1991 | Scott |
| 5,120,315 A | 6/1992 | Hessel |
| 5,147,311 A | 9/1992 | Pickhard |
| 5,163,928 A | 11/1992 | Hobbs et al. |
| 5,178,610 A | 1/1993 | Tsujikawa et al. |
| 5,192,272 A | 3/1993 | Faure |
| 5,199,567 A | 4/1993 | Discko, Jr. |
| 5,201,438 A | 4/1993 | Norwood |
| 5,209,372 A | 5/1993 | Norwood |
| 5,236,204 A | 8/1993 | Hempel |
| 5,237,309 A | 8/1993 | Frantz et al. |
| 5,238,003 A | 8/1993 | Baidwan et al. |
| 5,238,150 A | 8/1993 | Williams |
| 5,240,130 A | 8/1993 | Osbakk |
| 5,242,422 A | 9/1993 | Schneberger et al. |
| 5,263,940 A | 11/1993 | Kriesel |
| 5,269,428 A | 12/1993 | Gilbert |
| 5,312,018 A | 5/1994 | Evezich |
| 5,316,452 A | 5/1994 | Bogen et al. |
| 5,318,520 A | 6/1994 | Nakao |
| 5,318,540 A | 6/1994 | Athayde et al. |
| 5,333,761 A | 8/1994 | Davis et al. |
| 5,342,313 A | 8/1994 | Campbell et al. |
| 5,353,961 A | 10/1994 | Debush |
| 5,370,250 A | 12/1994 | Gilbert |

(56) References Cited

U.S. PATENT DOCUMENTS

| | | |
|---|---|---|
| 5,383,858 A | 1/1995 | Reilly et al. |
| 5,397,157 A | 3/1995 | Hempel et al. |
| 5,399,173 A | 3/1995 | Parks et al. |
| 5,431,185 A | 7/1995 | Shannon et al. |
| 5,492,147 A | 2/1996 | Challender et al. |
| 5,507,535 A | 4/1996 | McKamey et al. |
| 5,520,653 A | 5/1996 | Reilly et al. |
| 5,573,129 A | 11/1996 | Nagata et al. |
| 5,578,005 A | 11/1996 | Sancoff et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,651,776 A | 7/1997 | Appling et al. |
| 5,683,369 A | 11/1997 | Tsukada |
| 5,725,500 A | 3/1998 | Micheler |
| 5,758,789 A | 6/1998 | Shin et al. |
| 5,794,107 A | 8/1998 | Russell |
| 5,827,233 A | 10/1998 | Futagawa et al. |
| 5,836,922 A | 11/1998 | Hansen et al. |
| 5,873,861 A | 2/1999 | Hitchins et al. |
| 5,893,843 A | 4/1999 | Rodrigues Claro |
| 5,899,889 A | 5/1999 | Futagawa et al. |
| 5,935,105 A | 8/1999 | Manning et al. |
| 5,957,898 A | 9/1999 | Jepson et al. |
| RE36,377 E | 11/1999 | Gilbert |
| 5,976,112 A | 11/1999 | Lyza, Jr. |
| 5,979,326 A | 11/1999 | Ohinata |
| 5,980,489 A | 11/1999 | Kriesel |
| 5,984,378 A | 11/1999 | Ostrander et al. |
| 6,054,194 A | 4/2000 | Kane |
| 6,056,724 A | 5/2000 | Lacroix |
| 6,062,437 A | 5/2000 | Mascitelli |
| 6,063,058 A | 5/2000 | Sakamoto |
| 6,077,252 A | 6/2000 | Siegel |
| 6,105,815 A | 8/2000 | Mazda |
| 6,132,396 A | 10/2000 | Antanavich et al. |
| 6,142,976 A | 11/2000 | Kubo |
| 6,159,183 A | 12/2000 | Neer et al. |
| 6,177,049 B1 | 1/2001 | Schnell et al. |
| 6,216,915 B1 | 4/2001 | Harman et al. |
| 6,224,577 B1 | 5/2001 | Dedola et al. |
| 6,250,505 B1 | 6/2001 | Petit |
| 6,270,482 B1 | 8/2001 | Rosoff et al. |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,322,542 B1 | 11/2001 | Nilson et al. |
| 6,328,715 B1 | 12/2001 | Dragan et al. |
| 6,332,876 B1 | 12/2001 | Poynter et al. |
| 6,442,418 B1 | 8/2002 | Evans, III et al. |
| 6,450,993 B1 | 9/2002 | Lin |
| 6,465,024 B1 | 10/2002 | Di et al. |
| 6,485,471 B1 | 11/2002 | Zivitz et al. |
| 6,497,684 B2 | 12/2002 | Witowski et al. |
| 6,558,358 B2 | 5/2003 | Rosoff et al. |
| 6,575,930 B1 | 6/2003 | Trombley, III et al. |
| 6,578,738 B1 | 6/2003 | Keller |
| 6,616,000 B1 | 9/2003 | Renz |
| 6,620,134 B1 | 9/2003 | Trombley, III et al. |
| 6,634,524 B1 | 10/2003 | Helmenstein |
| 6,643,537 B1 | 11/2003 | Zatezalo et al. |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,723,074 B1 | 4/2004 | Halseth |
| 6,726,657 B1 | 4/2004 | Dedig et al. |
| 6,731,971 B2 | 5/2004 | Evans et al. |
| 6,773,417 B2 | 8/2004 | Fitzgibbons et al. |
| 6,840,164 B2 | 1/2005 | Eastman |
| 6,855,130 B2 | 2/2005 | Saulenas et al. |
| 6,866,039 B1 | 3/2005 | Wright et al. |
| 6,866,654 B2 | 3/2005 | Callan et al. |
| 6,869,419 B2 | 3/2005 | Dragan et al. |
| 6,921,384 B2 | 7/2005 | Reilly et al. |
| RE38,770 E | 8/2005 | Gilbert |
| 6,974,443 B2 | 12/2005 | Reilly et al. |
| 6,984,222 B1 | 1/2006 | Hitchins et al. |
| 7,004,213 B2 | 2/2006 | Hansen |
| 7,011,650 B2 | 3/2006 | Rosoff et al. |
| 7,094,216 B2 | 8/2006 | Trombley, III et al. |
| 7,101,352 B2 | 9/2006 | Duchon et al. |
| 7,192,416 B1 | 3/2007 | Azzaro et al. |
| 7,192,549 B2 | 3/2007 | Hansen |
| 7,240,926 B2 | 7/2007 | Dalle et al. |
| 7,250,039 B2 | 7/2007 | Fitzgerald |
| 7,309,463 B2 | 12/2007 | Hansen |
| 7,351,221 B2 | 4/2008 | Trombley, III et al. |
| 7,419,478 B1 | 9/2008 | Reilly et al. |
| 7,427,281 B2 | 9/2008 | Uber et al. |
| 7,457,804 B2 | 11/2008 | Uber, III et al. |
| 7,462,166 B2 | 12/2008 | Kowan et al. |
| 7,497,843 B1 | 3/2009 | Castillo et al. |
| 7,513,378 B2 | 4/2009 | Mori et al. |
| 7,540,856 B2 | 6/2009 | Hitchins et al. |
| 7,553,294 B2 | 6/2009 | Lazzaro et al. |
| 7,556,619 B2 | 7/2009 | Spohn et al. |
| 7,563,249 B2 | 7/2009 | Schriver et al. |
| 7,581,559 B2 | 9/2009 | Bausmith et al. |
| 7,597,683 B2 | 10/2009 | Myhrberg et al. |
| 7,604,623 B2 | 10/2009 | Brunner et al. |
| 7,611,503 B2 | 11/2009 | Spohn et al. |
| 7,621,395 B2 | 11/2009 | Mogensen et al. |
| 7,666,169 B2 | 2/2010 | Cowan et al. |
| 7,686,788 B2 | 3/2010 | Freyman et al. |
| 7,766,883 B2 | 8/2010 | Rellly et al. |
| 7,802,691 B2 | 9/2010 | Musalek et al. |
| 7,818,992 B2 | 10/2010 | Riley et al. |
| 7,861,893 B2 | 1/2011 | Voegele et al. |
| 7,996,381 B2 | 8/2011 | Uber, III et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,337,456 B2 | 12/2012 | Schriver et al. |
| 8,388,580 B2 | 3/2013 | Schriver et al. |
| 8,419,676 B2 | 4/2013 | Evans et al. |
| 8,439,863 B2 | 5/2013 | Fago et al. |
| 8,521,716 B2 | 8/2013 | Uber, III et al. |
| 8,540,698 B2 | 9/2013 | Spohn et al. |
| 8,740,877 B2 | 6/2014 | Borlaug et al. |
| 8,795,240 B2 | 8/2014 | Chelak |
| 8,872,708 B2 | 10/2014 | Hill et al. |
| 8,882,702 B2 | 11/2014 | Suchecki et al. |
| 8,882,708 B2 | 11/2014 | Hieb et al. |
| 8,919,384 B2 | 12/2014 | Spohn et al. |
| 8,945,051 B2 | 2/2015 | Schriver et al. |
| 8,992,489 B2 | 3/2015 | Spohn et al. |
| 9,173,995 B1 | 11/2015 | Tucker et al. |
| 9,180,252 B2 | 11/2015 | Gelblum et al. |
| 9,180,260 B2 | 11/2015 | Huang et al. |
| 9,199,033 B1 | 12/2015 | Cowan et al. |
| 9,474,857 B2 | 10/2016 | Riley et al. |
| 9,498,570 B2 | 11/2016 | Cowan et al. |
| 9,555,379 B2 | 1/2017 | Schriver et al. |
| 9,566,381 B2 | 2/2017 | Barron et al. |
| 9,649,436 B2 | 5/2017 | Capone et al. |
| 9,901,671 B2 | 2/2018 | Toews et al. |
| 10,022,493 B2 | 7/2018 | Shearer, Jr. et al. |
| 10,046,106 B2 | 8/2018 | Cowan et al. |
| 10,105,491 B2 | 10/2018 | Gelblum et al. |
| 10,124,110 B2 | 11/2018 | Dedig et al. |
| 10,188,849 B2 | 1/2019 | Fangrow |
| 10,201,666 B2 | 2/2019 | Cowan et al. |
| 10,398,353 B2 | 9/2019 | Addison et al. |
| 10,420,902 B2 | 9/2019 | Cowan et al. |
| 10,507,319 B2 | 12/2019 | Haury et al. |
| 10,549,084 B2 | 2/2020 | Sokolov et al. |
| 10,857,345 B2 | 12/2020 | Uber, III et al. |
| 10,933,190 B2 | 3/2021 | Berry et al. |
| 11,083,882 B2 | 8/2021 | Schrauder et al. |
| 11,207,462 B2 | 12/2021 | Cowan et al. |
| 11,389,585 B2 | 7/2022 | Spohn et al. |

(56) References Cited

U.S. PATENT DOCUMENTS

| | | |
|---|---|---|
| 11,547,793 B2 | 1/2023 | Cowan et al. |
| 2001/0004466 A1 | 6/2001 | Heinz et al. |
| 2001/0018575 A1 | 8/2001 | Lyza |
| 2002/0010596 A1 | 1/2002 | Matory |
| 2002/0147429 A1 | 10/2002 | Cowan et al. |
| 2003/0216695 A1 | 11/2003 | Yang |
| 2003/0226539 A1 | 12/2003 | Kim et al. |
| 2004/0068224 A1 | 4/2004 | Couvillon et al. |
| 2004/0092905 A1 | 5/2004 | Azzolini |
| 2004/0116893 A1 | 6/2004 | Spohn et al. |
| 2004/0154788 A1 | 8/2004 | Symonds |
| 2004/0186457 A1 | 9/2004 | Truitt et al. |
| 2004/0249344 A1 | 12/2004 | Nemoto et al. |
| 2004/0254541 A1 | 12/2004 | Wong et al. |
| 2005/0082828 A1 | 4/2005 | Wicks et al. |
| 2005/0113754 A1 | 5/2005 | Cowan |
| 2005/0121103 A1 | 6/2005 | Steigerwalt et al. |
| 2006/0052794 A1 | 3/2006 | McGill et al. |
| 2006/0149213 A1 | 7/2006 | Raybuck |
| 2007/0068964 A1 | 3/2007 | Tanaami et al. |
| 2007/0129705 A1 | 6/2007 | Trombley et al. |
| 2008/0045925 A1 | 2/2008 | Stepovich et al. |
| 2008/0146996 A1 | 6/2008 | Smisson et al. |
| 2009/0069792 A1 | 3/2009 | Frey et al. |
| 2009/0112087 A1 | 4/2009 | Fago |
| 2009/0216192 A1 | 8/2009 | Schriver et al. |
| 2009/0218243 A1 | 9/2009 | Gyrn et al. |
| 2010/0063445 A1 | 3/2010 | Sternberg et al. |
| 2010/0089475 A1 | 4/2010 | Tracey |
| 2010/0091361 A1 | 4/2010 | Yuuki |
| 2010/0114064 A1 | 5/2010 | Kalafut et al. |
| 2010/0286650 A1 | 11/2010 | Fitzgerald |
| 2011/0009826 A1 | 1/2011 | Lewis |
| 2011/0218434 A1 | 9/2011 | Ziemba et al. |
| 2011/0275988 A1 | 11/2011 | Davis et al. |
| 2011/0282196 A1 | 11/2011 | Martz |
| 2012/0020911 A1 | 1/2012 | Seliktar et al. |
| 2012/0101472 A1 | 4/2012 | Schroeder et al. |
| 2012/0178629 A1 | 7/2012 | Hudson et al. |
| 2012/0209111 A1 | 8/2012 | Cowan et al. |
| 2012/0217231 A1 | 8/2012 | Moore et al. |
| 2012/0245560 A1 | 9/2012 | Hochman |
| 2012/0253291 A1 | 10/2012 | Ivosevic et al. |
| 2013/0023048 A1 | 1/2013 | Kim et al. |
| 2013/0030291 A1 | 1/2013 | Lewis |
| 2013/0043273 A1 | 2/2013 | Lee et al. |
| 2013/0053774 A1 | 2/2013 | Kirkpatrick |
| 2013/0067416 A1 | 3/2013 | Barron et al. |
| 2013/0204130 A1 | 8/2013 | McArthur et al. |
| 2013/0211248 A1 | 8/2013 | Cowan et al. |
| 2013/0310756 A1 | 11/2013 | Whalley et al. |
| 2014/0124087 A1 | 5/2014 | Anderson et al. |
| 2014/0261713 A1 | 9/2014 | Schriver et al. |
| 2014/0276652 A1 | 9/2014 | Gittard |
| 2014/0374353 A1 | 12/2014 | Wright et al. |
| 2015/0260325 A1 | 9/2015 | Quick |
| 2016/0030662 A1 | 2/2016 | Uber, III et al. |
| 2016/0250409 A1 | 9/2016 | Dedig et al. |
| 2016/0346484 A1* | 12/2016 | Abal .................. A61M 5/365 |
| 2017/0035974 A1 | 2/2017 | Berry et al. |
| 2017/0100534 A1 | 4/2017 | Fukikoshi et al. |
| 2017/0165427 A1 | 6/2017 | Uber, III et al. |
| 2017/0232173 A1 | 8/2017 | Perry et al. |
| 2018/0280630 A1 | 10/2018 | Jiang et al. |
| 2018/0296755 A1 | 10/2018 | Dahlin et al. |
| 2019/0240424 A1 | 8/2019 | Yoshioka et al. |
| 2020/0164141 A1* | 5/2020 | Biermann .......... A61M 5/1413 |
| 2020/0206490 A1 | 7/2020 | Bae |
| 2020/0246541 A1 | 8/2020 | Neftel et al. |
| 2021/0023298 A1 | 1/2021 | McDermott et al. |
| 2021/0146064 A1 | 5/2021 | Knutsson |
| 2021/0193289 A1 | 6/2021 | Cowan et al. |
| 2021/0220561 A1 | 7/2021 | Spohn et al. |
| 2021/0316065 A1 | 10/2021 | Berry et al. |
| 2021/0353870 A1 | 11/2021 | Volkar et al. |
| 2023/0146744 A1 | 5/2023 | Cowan et al. |
| 2023/0181816 A1 | 6/2023 | Lee |

FOREIGN PATENT DOCUMENTS

| | | |
|---|---|---|
| EP | 0446898 A2 | 9/1991 |
| EP | 1086661 A2 | 3/2001 |
| EP | 1572266 A2 | 9/2005 |
| EP | 1769849 A1 | 4/2007 |
| EP | 1800704 A1 | 6/2007 |
| EP | 2005934 A2 | 12/2008 |
| EP | 2098258 A1 | 9/2009 |
| EP | 2692375 A1 | 2/2014 |
| EP | 2719420 A1 | 4/2014 |
| EP | 2754459 A1 | 7/2014 |
| EP | 2767299 A1 | 8/2014 |
| EP | 3057648 A1 | 8/2016 |
| EP | 2962770 B1 | 3/2017 |
| EP | 3248635 A1 | 11/2017 |
| FR | 1288915 A | 3/1962 |
| GB | 1173662 A | 12/1969 |
| GB | 2214819 A | 9/1989 |
| GB | 2374143 A | 10/2002 |
| JP | H02-88664 | 7/1990 |
| JP | H0849598 A | 2/1996 |
| JP | H10999034 A | 4/1997 |
| JP | 5485885 B2 | 5/2014 |
| JP | 5511409 B2 | 6/2014 |
| JP | 5882595 B2 | 3/2016 |
| JP | 5897798 B2 | 3/2016 |
| JP | 6552258 B2 | 7/2019 |
| JP | 6839853 B2 | 3/2021 |
| NO | 2021257667 A1 | 12/2021 |
| WO | 9221391 A1 | 12/1992 |
| WO | 9528195 A1 | 10/1995 |
| WO | 9707841 A2 | 3/1997 |
| WO | 0204049 A1 | 1/2002 |
| WO | 02066100 A2 | 8/2002 |
| WO | 2004033023 A1 | 4/2004 |
| WO | 2005035995 A1 | 4/2005 |
| WO | 2007133942 A2 | 11/2007 |
| WO | 2008050218 A2 | 5/2008 |
| WO | 2008153831 A2 | 12/2008 |
| WO | 2009038955 A1 | 3/2009 |
| WO | 2010004206 A2 | 1/2010 |
| WO | 2010014654 A1 | 2/2010 |
| WO | 2011011346 A1 | 1/2011 |
| WO | 2011125303 A1 | 10/2011 |
| WO | 2011129175 A1 | 10/2011 |
| WO | 2012061140 A1 | 5/2012 |
| WO | 2012155035 A1 | 11/2012 |
| WO | 2013043868 A1 | 3/2013 |
| WO | 2013043881 A1 | 3/2013 |
| WO | 2013043889 A1 | 3/2013 |
| WO | 2014027009 A1 | 2/2014 |
| WO | 2014055283 A1 | 4/2014 |
| WO | 2014160326 A1 | 10/2014 |
| WO | 2015058088 A1 | 4/2015 |
| WO | 2015066506 A2 | 5/2015 |
| WO | 2015164783 A1 | 10/2015 |
| WO | 2016058946 A1 | 4/2016 |
| WO | 2016069711 A1 | 5/2016 |
| WO | 2016069714 A1 | 5/2016 |
| WO | 2016112163 A1 | 7/2016 |
| WO | 2016157886 A1 | 10/2016 |
| WO | 2016172467 A1 | 10/2016 |
| WO | 2016190904 A1 | 12/2016 |
| WO | 2016191485 A1 | 12/2016 |
| WO | 2017040154 A1 | 3/2017 |
| WO | 2017091635 A1 | 6/2017 |
| WO | 2017091636 A1 | 6/2017 |
| WO | 2017091643 A1 | 6/2017 |
| WO | 2018053074 A1 | 3/2018 |
| WO | 2018057386 A1 | 3/2018 |
| WO | 2018218132 A1 | 11/2018 |
| WO | 2019046259 A1 | 3/2019 |
| WO | 2019046260 A1 | 3/2019 |
| WO | 2019046299 A1 | 3/2019 |

(56) References Cited

FOREIGN PATENT DOCUMENTS

| WO | 2019152978 A1 | 8/2019 |
| WO | 2019204605 A1 | 10/2019 |
| WO | 2019204617 A1 | 10/2019 |
| WO | 2020055785 A1 | 3/2020 |
| WO | 2020055818 A1 | 3/2020 |
| WO | 2021050507 A1 | 3/2021 |
| WO | 2021168076 A1 | 8/2021 |
| WO | 2021173743 A1 | 9/2021 |
| WO | 2021188416 A1 | 9/2021 |
| WO | 2021188460 A1 | 9/2021 |
| WO | 2021222619 A1 | 11/2021 |
| WO | 2021247595 A1 | 12/2021 |
| WO | 2021257699 A1 | 12/2021 |
| WO | 2022035791 A1 | 2/2022 |
| WO | 2022036058 A1 | 2/2022 |
| WO | 2022265695 A1 | 12/2022 |

OTHER PUBLICATIONS

International Preliminary Report on Patentability from PCT Application No. PCT/US2021/061201, mailed Jun. 15, 2023.
Un Haluk, A New Device Preventing Air Embolism During The Angiography, Air Trap Device: An In-Vitro Experimental Air Emboli Study, Proceedings of the 2019 Design of Medical Devices Conference, 2019.

* cited by examiner

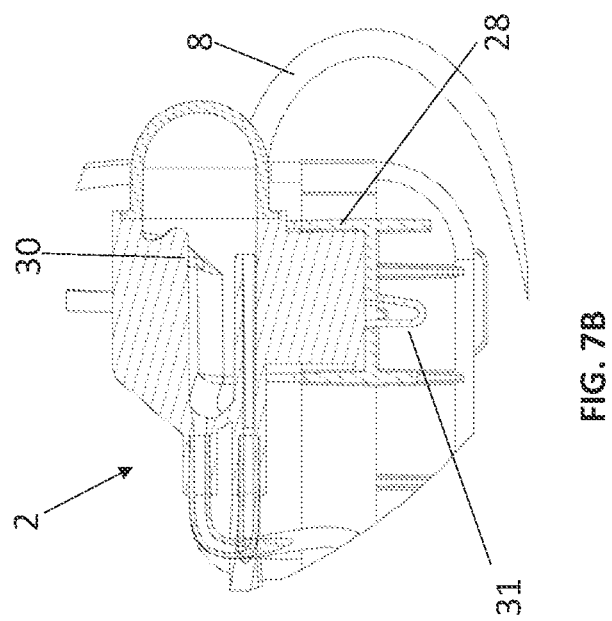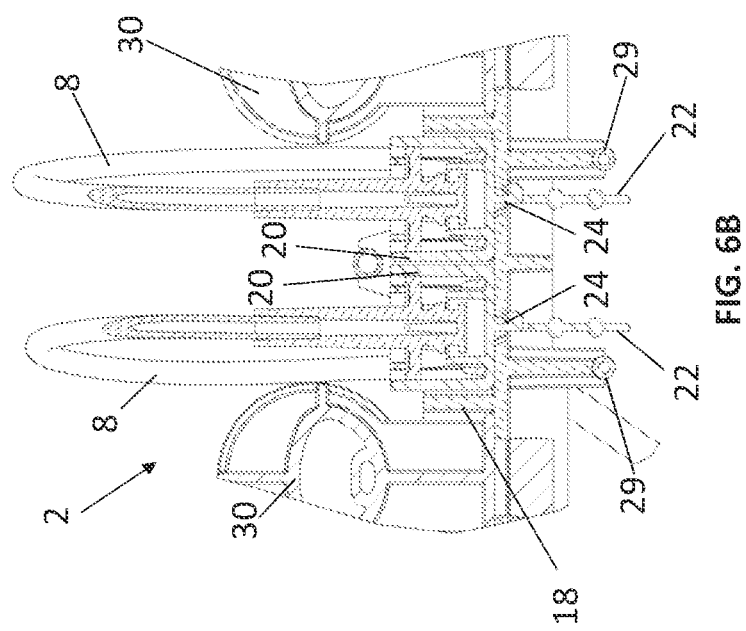

CASSETTE FOR RETENTION OF FLUID PATH COMPONENTS FOR FLUID INJECTOR SYSTEM

CROSS REFERENCE TO RELATED APPLICATIONS

This application is a U.S. national phase application under 35 U.S.C. § 371 of PCT International Application No. PCT/US2021/061201, filed 30 Nov. 2021, and claims the benefit of U.S. Provisional Patent Application No. 63/199,010, filed on 1 Dec. 2020, the disclosures of which are incorporated in their entirety by reference.

BACKGROUND OF THE INVENTION

Field of the Invention

The present disclosure is related generally to features associated with a cassette for retaining and managing fluid path components for a fluid injector system. The cassette allows easy and compact storage of the various fluid path components which can, in turn, be readily accessed and engaged to the fluid injector for utilization in a fluid injection procedure.

Description of Related Art

Syringe injection systems are among the medical devices used in medical imaging procedures. Many such syringes are operated manually by advancing a plunger extension in operative connection with an internal plunger to pressurize the fluid within the syringe. In numerous medical injection procedures, however, accurate control and/or high pressures may be required that cannot be achieved via manual syringe operation. A number of syringes and powered injectors for use therewith have, therefore, been developed for use in contrast enhanced medical imaging procedures such as angiography, computed tomography (CT), and nuclear magnetic resonance (NMR)/magnetic resonance imaging (MRI). For example, U.S. Pat. No. 5,383,858 discloses a front-loading syringe and powered injector in pressure jacket and jacketless configurations, the disclosure of which is incorporated herein by reference.

To load syringes with contrast fluid, a user typically connects a fill tube and/or spike to a front nozzle or discharge outlet of the syringe and places the other end of the tube/spike in a bottle or bag of contrast medium (hereinafter "contrast") or other fluid, such as saline or other flushing fluid. The plunger of the syringe is retracted (usually by means of the injector piston) to aspirate the contrast into the syringe until the desired amount is loaded into the syringe. After the syringe is filled, the syringe may be primed to remove air from the syringe and fluid path. The various fluid path components may then be connected to a patient catheter for the fluid injection protocol.

Conventional fluid injector systems may utilize multiple components in the fluid path during the filling and delivery procedures. These fluid path components include tubing and spikes and/or connectors for filling the syringe from the bulk fluid sources for contrast and saline and for delivery of fluid from the syringe to the patient, air management components, valves, and stopcocks for managing fluid flow through the fluid path components, sterility maintaining components, and the like. For example, in certain cases, significant lengths of tubing are used and can become tangled during shipping and set-up. Apparatuses for managing the various fluid path components which allow for rapid access and set up are needed. The loose tubing may also be installed correctly due to the excessive length of the tubing that may be loose relative to the fluid injector.

SUMMARY OF THE INVENTION

In one embodiment, a cassette for holding fluid path components for a fluid injector, the cassette may include a body defining at least one feature for holding at least one fluid path component for the fluid injector; and a connecting member for removably connecting the body of the cassette to a receiving surface of the fluid injector, the connecting member operatively connected to the body, wherein the connecting member comprises at least one pivotable connecting feature protruding from the body, and wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body of the cassette is positioned for operative connection to a corresponding feature of the fluid injector.

In another embodiment, the at least one fluid path component is selected from at least one of at least one stopcock, at least one air bubble suspension apparatus, one or more fluid line components, at least one fluid path components comprising an air detection region, and at least one removable end cap for a fluid line. The at least one feature of the body is at least one extension member that protrudes from the body, wherein the at least one extension member is configured to hold a fluid path component of the fluid injector. The at least one extension member includes a retaining tab for holding the fluid path component on the at least one extension member. The at least one extension member comprises a plurality of extension members, each extension member configured to hold at least one fluid path component of the fluid injector. The at least one fluid component comprises at least one stopcock, wherein the stopcock comprises a first fluid filling position providing fluid communication between a bulk fluid container and a syringe engaged to the fluid injector, a second fluid delivery position providing fluid communication between the syringe and a patient tubing set, and a third stopped position blocking fluid communication between the syringe, the bulk fluid container, and the patient tubing set, and wherein the at least one extension member retains the at least one stopcock in a position configured to engage at least one stopcock actuator of the fluid injector when the cassette is in the second latched position. The stopcock actuator actuates the stopcock between the first fluid filling position, the second fluid delivery position, and the third stopped position is response to a signal from a controller of the fluid injector. The body further comprises a shield member that prevents a user from accessing at least one stopcock held in the body of the cassette. The at least one fluid component comprises at least one air bubble suspension apparatus fluidly located between the at least one fluid path components comprising the air detection region and the at least one stopcock, wherein at least one retention element retains the at least one air bubble suspension apparatus in a position to be movable between a first priming position and a second injection position with movement of a head of the fluid injector between an upright priming position and a downward angled injection position. The at least one air bubble suspension apparatus is configured to prime substantially all air bubbles out of the at least one air bubble suspension apparatus when primed in the upright priming position; and configured to at least temporarily suspend any air bubble detected in an injection fluid during a fluid injection procedure when in the downward angled injection position. The at least one fluid component comprises at least one fluid path components comprising an air detection region, wherein at least one retention element retains the at least one fluid path components comprising an air detection region in a position to operatively engage an air detector on the receiving surface of the fluid detector. The air detector is configured to detect an air bubble in an injection fluid during a fluid injection procedure, and in response to detecting an air bubble in the injection fluid, send a signal to the controller of the fluid injector to cause the at least one stopcock actuator to move the at least one stopcock from the second fluid delivery position, and the third stopped position. The at least one fluid component comprises at least one removable end cap for the fluid line, wherein the at least one removable end cap covers and prevents inadvertent contamination of a connector element of the fluid line. The cassette comprises two stopcocks, two air bubble suspension apparatuses, a plurality of fluid line components, two fluid path components each comprising an air detection region, and a plurality of removable end caps from the fluid line. The connecting member comprises a locking tab that is configured to be received in a corresponding locking groove on the fluid injector for removably attaching the receiving surface to the fluid injector. The connecting member comprises a latch member configured to removably connect with a locking arm on the fluid injector. An identifier may be positioned on the body, the identifier configured to provide information regarding the cassette including at least one of date of assembly, number of uses of the cassette, and location of the cassette. The identifier may comprise a barcode.

In another embodiment, a fluid injector may include a housing; at least one syringe removably held in the housing; and a cassette for holding fluid path components for a fluid injector, the cassette comprising: a body defining at least one feature for holding at least one fluid path component for the fluid injector; and a connecting member for removably connecting the body of the cassette to the fluid injector, the connecting member operatively connected to the body, wherein the connecting member comprises at least one pivotable connecting feature protruding from the body, and wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body of the cassette is positioned for operative connection to a corresponding feature of the fluid injector.

In another embodiment, the at least one fluid path component is selected from at least one of at least one stopcock, at least one air bubble suspension apparatus, one or more fluid line components, at least one fluid path components comprising an air detection region, and at least one removable end cap for a fluid line. The at least one feature of the body is at least one extension member that protrudes from the body, wherein the at least one extension member is configured to hold a fluid path component of the fluid injector. The at least one extension member includes a retaining tab for holding the fluid path component on the at least one extension member. The body of the cassette may comprise a plurality of retention elements, each retention element configured to hold at least one fluid path component of the fluid injector. The at least one fluid component comprises at least one stopcock, wherein the stopcock comprises a first fluid filling position providing fluid communication between a bulk fluid container and a syringe engaged to the fluid injector, a second fluid delivery position providing fluid communication between the syringe and a patient tubing set, and a third stopped position blocking fluid communication between the syringe, the bulk fluid container, and the patient tubing set, and wherein the at least one retention element retains the at least one stopcock in a position configured to engage at least one stopcock actuator of the fluid injector when the cassette is in the second latched position. The stopcock actuator actuates the stopcock between the first fluid filling position, the second fluid delivery position, and the third stopped position is response to a signal from a controller of the fluid injector. The body further comprises a shield member that prevents a user from accessing at least one stopcock held in the body of the cassette. The at least one fluid component comprises at least one air bubble suspension apparatus fluidly located between the at least one fluid path components comprising the air detection region and the at least one stopcock, wherein the at least one retention element retains the at least one air bubble suspension apparatus in a position to be movable between a first priming position and a second injection position with movement of a head of the fluid injector between an upright priming position and a downward angled injection position. The at least one air bubble suspension apparatus is configured to prime substantially all air bubbles out of the at least one air bubble suspension apparatus when primed in the upright priming position; and configured to at least temporarily suspend any air bubble detected in an injection fluid during a fluid injection procedure when in the downward angled injection position. The at least one fluid component comprises at least one fluid path components comprising an air detection region, wherein the at least one retention element retains the at least one fluid path components comprising an air detection region in a position to operatively engage an air detector on a cassette receiving surface of the fluid detector. The air detector is configured to detect an air bubble in an injection fluid during a fluid injection procedure, and in response to detecting an air bubble in the injection fluid, send a signal to the controller of the fluid injector to cause the at least one stopcock actuator to move the at least one stopcock from the second fluid delivery position, and the third stopped position. The at least one fluid component comprises at least one removable end cap for the fluid line, wherein the at least one removable end cap covers and prevents inadvertent contamination of a connector element of the fluid line. The cassette comprises two stopcocks, two air bubble suspension apparatuses, a plurality of fluid line components, two fluid path components each comprising an air detection region, and a plurality of removable end caps from the fluid line. The connecting member comprises a locking tab that is configured to be received in a corresponding locking groove on the fluid injector for removably attaching the body to the fluid injector. The connecting member comprises a latch member configured to removably connect with a locking arm on the fluid injector. An identifier may be positioned on the body, the identifier configured to provide information regarding the cassette including at least one of date of assembly, number of uses of the cassette, and location of the cassette. The identifier may comprise a barcode.

In another embodiment, a method of attaching at least one component to a fluid injector may include attaching the at least one component to a cassette, the cassette comprising a body defining at least one aperture for holding the at least one component, and a connecting member operatively connected to the body; and connecting the cassette to a housing of the fluid injector by operatively connecting the connecting member of the cassette to a corresponding connecting member on the fluid injector, wherein the connection of the cassette to the housing of the fluid injector is configured to position the at least one component at a predetermined location on the housing of the fluid injector.

In another embodiment, the at least one component is at least one of a stopcock, an air bubble suspension apparatus, a fluid line, and a dust cap for a fluid line. The method may include evaluating an identifier attached to the cassette to determine whether the cassette has already been used.

In another embodiment, a connection interface between a cassette and fluid injector, the cassette configured to hold at least one component of the fluid injector, the connection interface may include a first connecting member provided on the cassette that engages the fluid injector; and a second connecting member provided on the fluid injector that receives the first connecting member, wherein a connection of the first connecting member to the second connecting member is configured to position the at least one component at a predetermined location on the fluid injector.

Embodiments of the present invention is also disclosed in the following clauses:

Clause 1: A cassette for holding fluid path components for a fluid injector, the cassette comprising: a body defining at least one feature for holding at least one fluid path component for the fluid injector; and a connecting member for removably connecting the body of the cassette to the fluid injector, the connecting member operatively connected to the body, wherein the connecting member comprises at least one pivotable connecting feature protruding from the body, and wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body of the cassette is positioned for operative connection to a corresponding feature of the fluid injector.

Clause 2: The cassette of Clause 1, wherein the at least one fluid path component is selected from at least one of at least one stopcock, at least one air bubble suspension apparatus, one or more fluid line components, at least one fluid path components comprising an air detection region, and at least one removable end cap for a fluid line.

Clause 3: The cassette of Clause 1 or 2, wherein the at least one feature of the body is at least one extension member that protrudes from the body, wherein the at least one extension member is configured to hold a fluid path component of the fluid injector.

Clause 4: The cassette of Clause 3, wherein the at least one extension member includes a retaining tab for holding the fluid path component on the at least one extension member.

Clause 5: The cassette of Clause 3 or Clause 4, wherein the cassette comprises a plurality of retention elements, each retention element configured to hold a fluid path component of the fluid injector.

Clause 6: The cassette of any of Clauses 3 to 5, wherein the at least one fluid component comprises at least one stopcock, wherein the stopcock comprises a first fluid filling position providing fluid communication between a bulk fluid container and a syringe engaged to the fluid injector, a second fluid delivery position providing fluid communication between the syringe and a patient tubing set, and a third stopped position blocking fluid communication between the syringe, the bulk fluid container, and the patient tubing set, and wherein the at least one retention element retains the at least one stopcock in a position configured to engage at least one stopcock actuator of the fluid injector when the cassette is in the second latched position.

Clause 7: The cassette of Clause 6, wherein the stopcock actuator actuates the stopcock between the first fluid filling position, the second fluid delivery position, and the third stopped position is response to a signal from a controller of the fluid injector.

Clause 8: The cassette of any of Clauses 1 to 7, wherein the body further comprises a shield member that prevents a user from accessing at least one stopcock held in the body of the cassette.

Clause 9: The cassette of any of Clauses 3 to 5, wherein the at least one fluid component comprises at least one air bubble suspension apparatus fluidly located between the at least one fluid path components comprising the air detection region and the at least one stopcock, wherein the at least one retention element retains the at least one air bubble suspension apparatus in a position to be movable between a first priming position and a second injection position with movement of a head of the fluid injector between an upright priming position and a downward angled injection position.

Clause 10: The cassette of Clause 9, wherein the at least one air bubble suspension apparatus is configured to prime substantially all air bubbles out of the at least one air bubble suspension apparatus when primed in the upright priming position; and configured to at least temporarily suspend any air bubble detected in an injection fluid during a fluid injection procedure when in the downward angled injection position.

Clause 11: The cassette of any of Clauses 3 to 10, wherein the at least one fluid component comprises at least one fluid path components comprising an air detection region, wherein the at least one retention element retains the at least one fluid path components comprising an air detection region in a position to operatively engage an air detector on receiving surface of the fluid detector.

Clause 12: The cassette of Clause 11, wherein the air detector is configured to detect an air bubble in an injection fluid during a fluid injection procedure, and in response to detecting an air bubble in the injection fluid, send a signal to the controller of the fluid injector to cause the at least one stopcock actuator to move the at least one stopcock from the second fluid delivery position, and the third stopped position.

Clause 13: The cassette of any of Clauses 3 to 12, wherein the at least one fluid component comprises at least one removable end cap for the fluid line, wherein the at least one removable end cap covers and prevents inadvertent contamination of a connector element of the fluid line.

Clause 14: The cassette of any of Clauses 1 to 13, wherein the cassette comprises two stopcocks, two air bubble suspension apparatuses, a plurality of fluid line components, two fluid path components each comprising an air detection region, and a plurality of removable end caps from the fluid line.

Clause 15: The cassette of any of Clauses 1 to 14, wherein the connecting member comprises a locking tab that is configured to be received in a corresponding locking groove on the fluid injector for removably attaching the body to the fluid injector.

Clause 16: The cassette of any of Clauses 1 to 14, wherein the connecting member comprises a latch member configured to removably connect with a locking arm on the fluid injector.

Clause 17: The cassette of any of Clauses 1 to 16, further comprising an identifier positioned on the body, the identifier configured to provide information regarding the cassette including at least one of date of assembly, number of uses of the cassette, and location of the cassette.

Clause 18: The cassette of Clause 17, wherein the identifier comprises a barcode.

Clause 19: A fluid injector, comprising: a housing; at least one syringe removably held in the housing; and a cassette for holding fluid path components for a fluid injector, the cassette comprising: a body defining at least one feature for holding at least one fluid path component for the fluid injector; and a connecting member for removably connecting the body of the cassette to the fluid injector, the connecting member operatively connected to the body, wherein the connecting member comprises at least one pivotable connecting feature protruding from the body, and wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body of the cassette is positioned for operative connection to a corresponding feature of the fluid injector.

Clause 20: The fluid injector of Clause 19, wherein the at least one fluid path component is selected from at least one of at least one stopcock, at least one air bubble suspension apparatus, one or more fluid line components, at least one fluid path components comprising an air detection region, and at least one removable end cap for a fluid line.

Clause 21: The fluid injector of Clause 19 or 20, wherein the at least one feature of the body is at least one extension member that protrudes from the body, wherein the at least one extension member is configured to hold a fluid path component of the fluid injector.

Clause 22: The fluid injector of Clause 21, wherein the at least one extension member includes a retaining tab for holding the fluid path component on the at least one extension member.

Clause 23: The fluid injector of Clause 21 or Clause 22, wherein the cassette comprises a plurality of retention elements, each retention element configured to hold a fluid path component of the fluid injector.

Clause 24: The fluid injector of any of Clauses 21 to 23, wherein the at least one fluid component comprises at least one stopcock, wherein the stopcock comprises a first fluid filling position providing fluid communication between a bulk fluid container and a syringe engaged to the fluid injector, a second fluid delivery position providing fluid communication between the syringe and a patient tubing set, and a third stopped position blocking fluid communication between the syringe, the bulk fluid container, and the patient tubing set, and wherein the at least one retention element retains the at least one stopcock in a position configured to engage at least one stopcock actuator of the fluid injector when the cassette is in the second latched position.

Clause 25: The fluid injector of Clause 24, wherein the stopcock actuator actuates the stopcock between the first fluid filling position, the second fluid delivery position, and the third stopped position is response to a signal from a controller of the fluid injector.

Clause 26: The fluid injector of any of Clauses 19 to 25, wherein the body further comprises a shield member that prevents a user from accessing at least one stopcock held in the body of the cassette.

Clause 27: The fluid injector of any of Clauses 21 to 23, wherein the at least one fluid component comprises at least one air bubble suspension apparatus fluidly located between the at least one fluid path components comprising the air detection region and the at least one stopcock, wherein the at least one retention element retains the at least one air bubble suspension apparatus in a position to be movable between a first priming position and a second injection position with movement of a head of the fluid injector between an upright priming position and a downward angled injection position.

Clause 28: The fluid injector of Clause 27, wherein the at least one air bubble suspension apparatus is configured to prime substantially all air bubbles out of the at least one air bubble suspension apparatus when primed in the upright priming position; and configured to at least temporarily suspend any air bubble detected in an injection fluid during a fluid injection procedure when in the downward angled injection position.

Clause 29: The fluid injector of any of Clauses 21 to 28, wherein the at least one fluid component comprises at least one fluid path components comprising an air detection region, wherein the at least one retention element retains the at least one fluid path components comprising an air detection region in a position to operatively engage an air detector on a receiving surface of the fluid detector.

Clause 30: The fluid injector of Clause 29, wherein the air detector is configured to detect an air bubble in an injection fluid during a fluid injection procedure, and in response to detecting an air bubble in the injection fluid, send a signal to the controller of the fluid injector to cause the at least one stopcock actuator to move the at least one stopcock from the second fluid delivery position, and the third stopped position.

Clause 31: The fluid injector of any of Clauses 21 to 30, wherein the at least one fluid component comprises at least one removable end cap for the fluid line, wherein the at least one removable end cap covers and prevents inadvertent contamination of a connector element of the fluid line.

Clause 32: The fluid injector of any of Clauses 19 to 31, wherein the cassette comprises two stopcocks, two air bubble suspension apparatuses, a plurality of fluid line components, two fluid path components each comprising an air detection region, and a plurality of removable end caps from the fluid line.

Clause 33: The fluid injector of any of Clauses 19 to 32, wherein the connecting member comprises a locking tab that is configured to be received in a corresponding locking groove on the fluid injector for removably attaching the body to the fluid injector.

Clause 34: The fluid injector of any of Clauses 19 to 32, wherein the connecting member comprises a latch member configured to removably connect with a locking arm on the fluid injector.

Clause 35: The fluid injector of any of Clauses 19 to 34, further comprising an identifier positioned on the body, the identifier configured to provide information regarding the cassette including at least one of date of assembly, number of uses of the cassette, and location of the cassette.

Clause 36: The fluid injector of Clause 35, wherein the identifier comprises a barcode.

Clause 37: A method of attaching at least one component to a fluid injector, the method comprising: attaching the at least one component to a cassette, the cassette comprising a body defining at least one aperture for holding the at least one component, and a connecting member operatively connected to the body; and connecting the cassette to a housing of the fluid injector by operatively connecting the connecting member of the cassette to a corresponding connecting member on the fluid injector, wherein the connection of the cassette to the housing of the fluid injector is configured to position the at least one component at a predetermined location on the housing of the fluid injector.

Clause 38: The method of Clause 37, wherein the at least one component is at least one of a stopcock, a bubble suspension apparatus, a fluid line, and a dust cap for a fluid line.

Clause 39: The method of Clause 37 or Clause 38, further comprising evaluating an identifier attached to the cassette to determine whether the cassette has already been used.

Clause 40: A connection interface between a cassette and fluid injector, the cassette configured to hold at least one component of the fluid injector, the connection interface comprising: a first connecting member provided on the cassette that engages the fluid injector; and a second connecting member provided on the fluid injector that receives the first connecting member, wherein a connection of the first connecting member to the second connecting member is configured to position the at least one component at a predetermined location on the fluid injector.

BRIEF DESCRIPTION OF THE DRAWINGS

The various features described herein are set forth with particularity in the appended claims. Such features, however, both as to organization and methods of operation may be better understood by reference to the following description, taken in conjunction with the accompanying drawings.

FIGS. 6A and 6B are cross-sectional views of the proximal end of the cassette of FIG. 4 showing dust cap connection to the cassette without tubing and connector elements (FIG. 6A) and with tubing and connector elements (FIG. 6B).

FIGS. 7A and 7B are cross-sectional views of the cassette of FIG. 4 showing a bubble suspension apparatus connection to the cassette along the longitudinal axis (FIG. 7A) and the lateral axis (FIG. 7B).

FIG. 16A illustrates the cassette assembly in the initial engagement position, FIG. 16B illustrates an intermediate position, and FIG. 16C illustrates a loaded position of the cassette assembly.

DESCRIPTION OF THE DISCLOSURE

Figure 1:
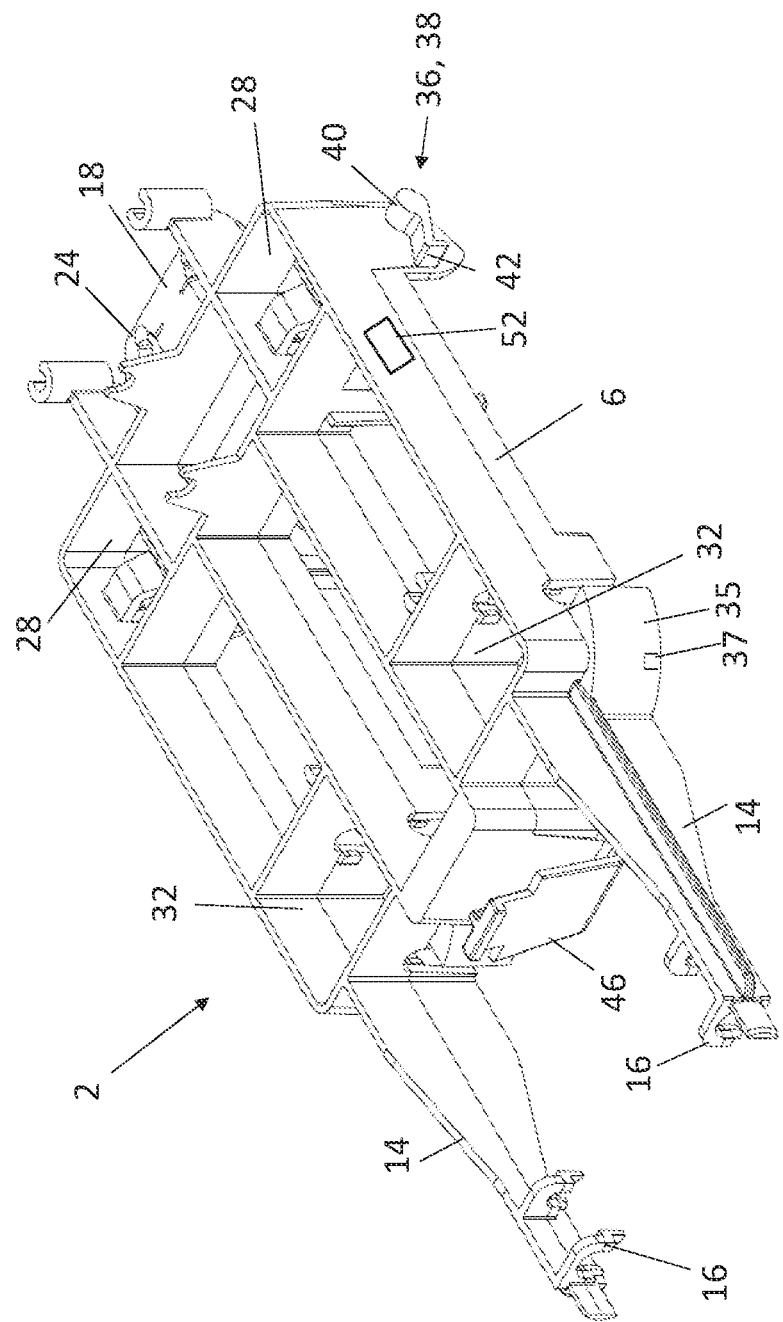
FIG. 1 is a perspective view of a cassette for a fluid injector according to a non-limiting embodiment of the present disclosure.
Figure 2:
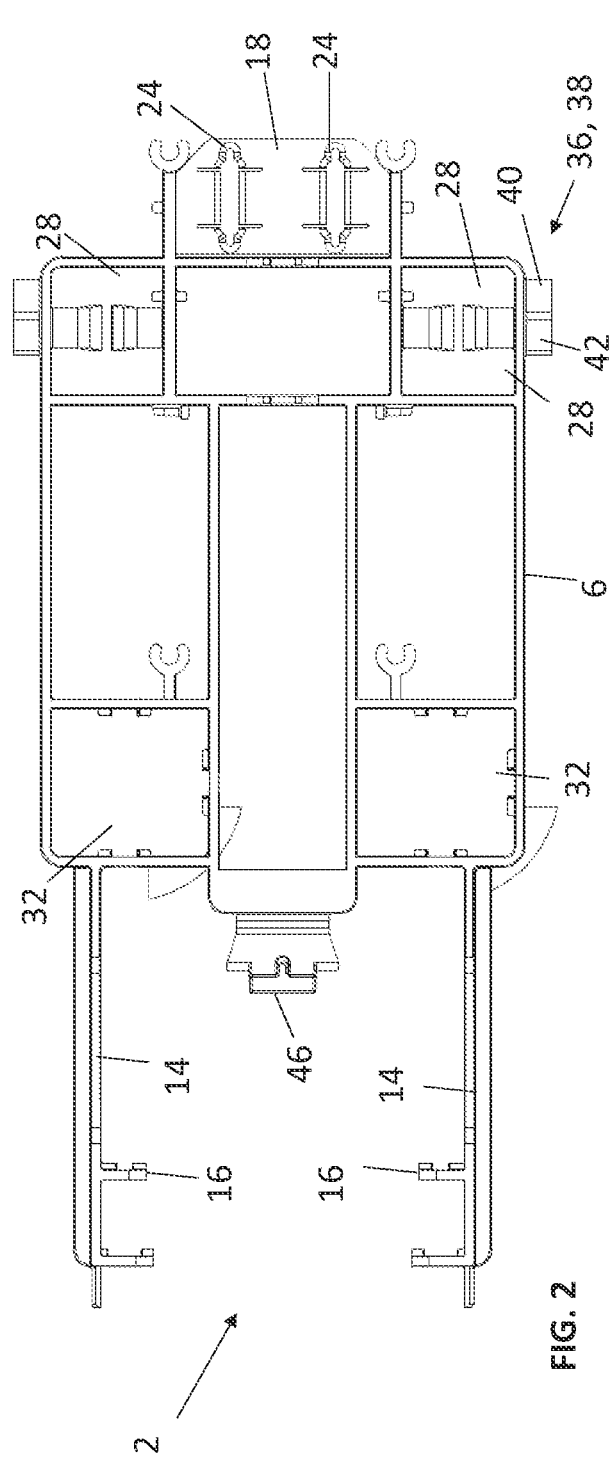
FIG. 2 is a top view of the cassette of FIG. 1.
Figure 3:
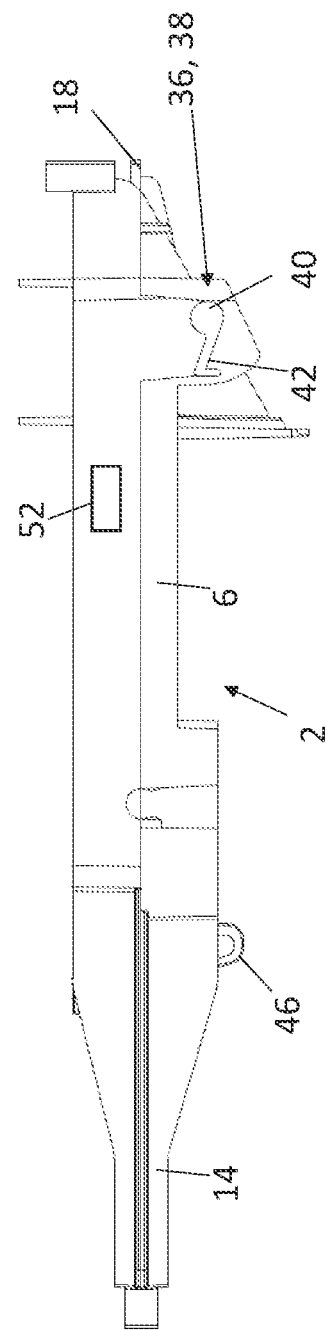
FIG. 3 is a side view of the cassette of FIG. 1.

In the following detailed description, reference is made to the accompanying drawings, which form a part hereof. The illustrative features shown and described in the detailed description, drawings, and claims are not meant to be limiting. Other features may be utilized, and other changes may be made, without departing from the scope of the subject matter presented here.

Before describing the various aspects of the cassette, the interaction with injector components, and various features thereof in detail, it should be noted that the various aspects disclosed herein are not limited in their application or use to the details of construction and arrangement of parts illustrated in the accompanying drawings and description. Rather, the disclosed devices may be positioned or incorporated in other devices, variations, and modifications thereof, and may be practiced or carried out in various ways. Accordingly, aspects of the cassette and fluid injector features disclosed herein are illustrative in nature and are not meant to limit the scope or application thereof. Furthermore, unless otherwise indicated, the terms and expressions employed herein have been chosen for the purpose of describing the various aspects of the cassette and fluid injector features for the convenience of the reader and are not to limit the scope thereof. In addition, it should be understood that any one or more of the components of the cassette and fluid injector features, expressions thereof, and/or examples thereof, can be combined with any one or more of the other components, expressions thereof, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects of the cassette and fluid injector features will be described in more detail with reference to the drawings.

With references to FIGS. 1-5, a disposable cassette 2 that simplifies installation of the disposable fluid path components on a powered medical fluid injector 4, such as a fluid injector for use in contrast enhanced angiography (CV), computed tomography (CT), magnetic resonance imaging (MRI), positron emission tomography (PET), ultrasound, and similar imaging procedures is shown and described. The cassette may include skeletal features, such as retention elements, for holding various fluid path components, for example in the appropriate position for alignment and interaction with various components of the fluid injector head, patient fluid lines, and/or bulk fluid sources. The various fluid path components may be held in the appropriate position and orientation by one or more retention elements. According to various embodiments, the cassette and various fluid path components may be manufactured and assembled at a production facility, treated to a sterilization process, and packaged for shipping to the end user. According to various embodiments, the cassette and fluid path components may be utilized as a multi-patient fluid path set, that may be used over a series of fluid injection procedures alone with a plurality of separate single-patient fluid path components that may be used for each injection procedure and disposed of before a subsequent fluid injection procedure. In other embodiments, the cassette and fluid path components may be utilized in a single use manner where the cassette and fluid path components are disposed of after a single injection procedure and a new cassette/fluid path components assembly are installed for the subsequent injection.

The cassette and fluid path component assembly may be configured for ready installation onto a receiving surface on a head of a fluid injector, as described herein. Thus, the cassette assembly may be designed to minimize time between injection procedures, allowing more injection procedures to be performed over a period of time. In addition, the cassette may reduce or eliminate user set-up error, since all fluid path components are assembled in the correct position and alignment, and the cassette may engage the receiving surface of the fluid injector in only a single possible orientation.

According to one embodiment of the present disclosure, the disposable cassette 2 simplifies installation of the disposable fluid path components on a fluid injector, such as, but not limited to, CV injector 4 (FIG. 10), by consolidating attachment points of the cassette and fluid path components with corresponding features on the fluid injector 4, while maintaining the various fluid path components in an organized and compact configuration. The cassette 2 may be used to simplify and manage the fluid path components such as by orienting the various components for example, one or more of properly inserting air detection regions of a fluid path component into air detectors associated with the fluid injector, mounting and orienting an air bubble suspension apparatus into a position to allow priming and/or bubble suspension, inserting a stopcock into a corresponding stopcock actuator on a fluid injector, properly inserting one or more compressible pinch valve region of a fluid path component into one or more corresponding pinch clamps on a fluid injector, managing tubing or other fluid path components, managing male or female connector components and/or spikes at the end of a fluid path in the proper orientation and/or proximity for connecting with a corresponding female or male connector component of a fluid injector component or fluid path component, and managing one or more removable end caps for a fluid line. The cassette 2 may be provided to the user as a single apparatus or scaffold having the various fluid path components located or connected to appropriate positions on the cassette 2 to allow ready installation of the cassette 2 and associated fluid path components onto a receiving surface 11 of the fluid injector 4 in a single action or a simple sequence of actions. The single action or simple sequence of actions of installing the cassette 2 replaces several complex actions of installing multiple fluid path components onto a conventional fluid injector; minimizing the possibility of incorrect installation of one or more of the multiple fluid path components which could lead to error in a fluid injection procedure. The cassette 2 may also be designed to only install in a single predetermined orientation relative to the fluid injector 4, thereby minimizing confusion, delay, and errors during setup and ensuring that various fluid path components are properly located for rapid connection to one or more syringes attached to the fluid injector 4.

According to one embodiment the present disclosure, the cassette 2 may include a body 6 configured to hold the various fluid path components in a position for operative connection with corresponding features of the fluid injector 4, disposable components, such as a syringe, attached thereto, and/or components attachable to the cassette fluid path components, such as a patient fluid line, a bulk fluid source, etc. The body 6 may define various apertures, compartments, and multiple retention elements for holding the various fluid path components. In one example, the cassette 2 is configured to hold at least one fluid line 8 that is used to deliver a medical fluid from the fluid injector 4 (i.e., a syringe on the fluid injector 4) to the patient. In one example, the cassette 2 may be configured to hold two separate fluid lines 8, in which each fluid line 8 is configured to deliver a different medical fluid to the patient. For example, one fluid line 8 may deliver a saline solution to the patient, while the other fluid line 8 may deliver a contrast media or other liquid medication formulation to the patient.

According to some embodiments of the present disclosure, the cassette 2 may include multiple features for mounting different tubing types thereon. According to various embodiments, cassette 2 may operatively hold fluid path components, such as fluid lines 8 which may include fill tubing, patient line tubing, and other fluid path components (see for example U.S. Provisional Application Nos. 63/212, 055, filed 17 Jun. 2021; and 63/222,605, filed 16 Jul. 2021, and PCT International Application Nos. PCT/US2021/

018523, filed 18 Feb. 2021; PCT/US2021/022421, filed 15 Mar. 2021; PCT/US2021/022321, filed 15 Mar. 2021; PCT/US2021/029963, filed 29 Apr. 2021; and PCT/US2021/01507, filed 25 Feb. 2021), in-line air bubble suspension components (PCT/US2021/037623, filed 16 Jun. 2021) and priming/purging tubing (PCT/US2021/045689, filed 13 Aug. 2021), the disclosure of each of which are incorporated in their entirety by this reference. In various embodiments, the cassette 2 may be designed for a single syringe set-up (e.g., where only contrast media is injected) or as a dual syringe set-up (e.g., including a first syringe containing contrast media and a second syringe containing a flushing fluid, such as saline or Ringer's lactate). According to embodiments, a single set of features could be used for all of these, or separate features for each fluid line 8.

Figure 17:
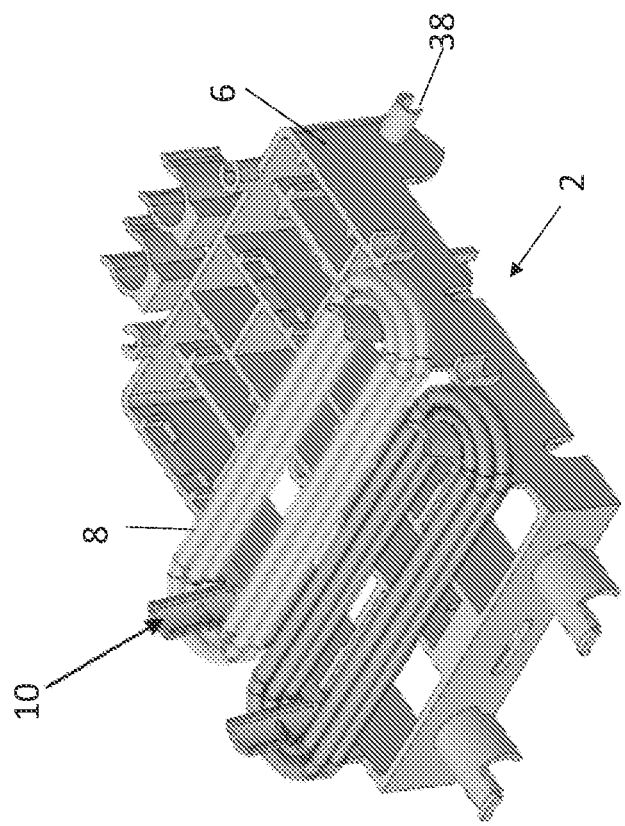
FIG. 17 is a perspective view of a cassette including posts for holding fluid lines on the cassette according to an embodiment of the present disclosure.
Figure 18:
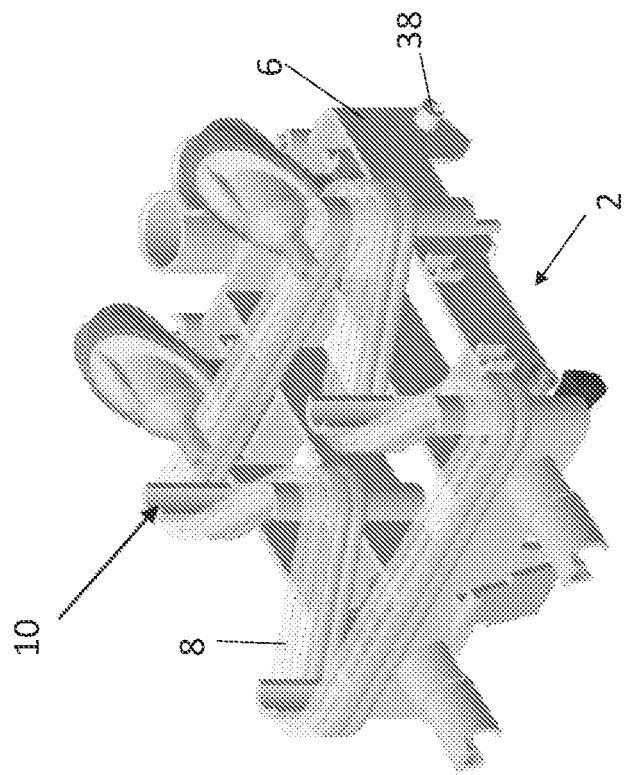
FIG. 18 is a perspective view of a cassette including angled posts for holding fluid lines on the cassette according to an embodiment of the present disclosure.

In specific embodiments for example as illustrated in FIGS. 17 and 18, one or more posts 10 may protrude from a surface of the cassette 2 for the fluid lines 8 to be wound around. For example, the longer patient fluid line 8 may be wound or otherwise engaged with the one or more posts to maintain the patient fluid line 8 in a compact position to minimize tangling during shipment and/or set up for a fluid injection. The one or more posts 10 may be designed to apply a spring force on the fluid lines 8, in certain embodiments, to ensure tension on the fluid lines 8 when held on the posts 10. The posts 10 and/or cassette 2 may also have one or more grooves or protrusions for the fluid lines 8 to be placed when retained on the posts 10. In certain embodiments, a lid or cap (not shown) may be placed on one or more post 10 or on all posts 10 to retain the fluid lines 8. The lid could be removable or permanently attached. In one non-limiting embodiment of the present disclosure, the posts 10 may be angled outwardly to create a tension on the fluid lines 8 wrapped around the posts 10. Fluid lines that may be associated with the one or more posts 10 may include the patient fluid line and/or the bulk fluid lines, for example with or without an associated spiking member for spiking a bulk fluid source.

Figure 4:
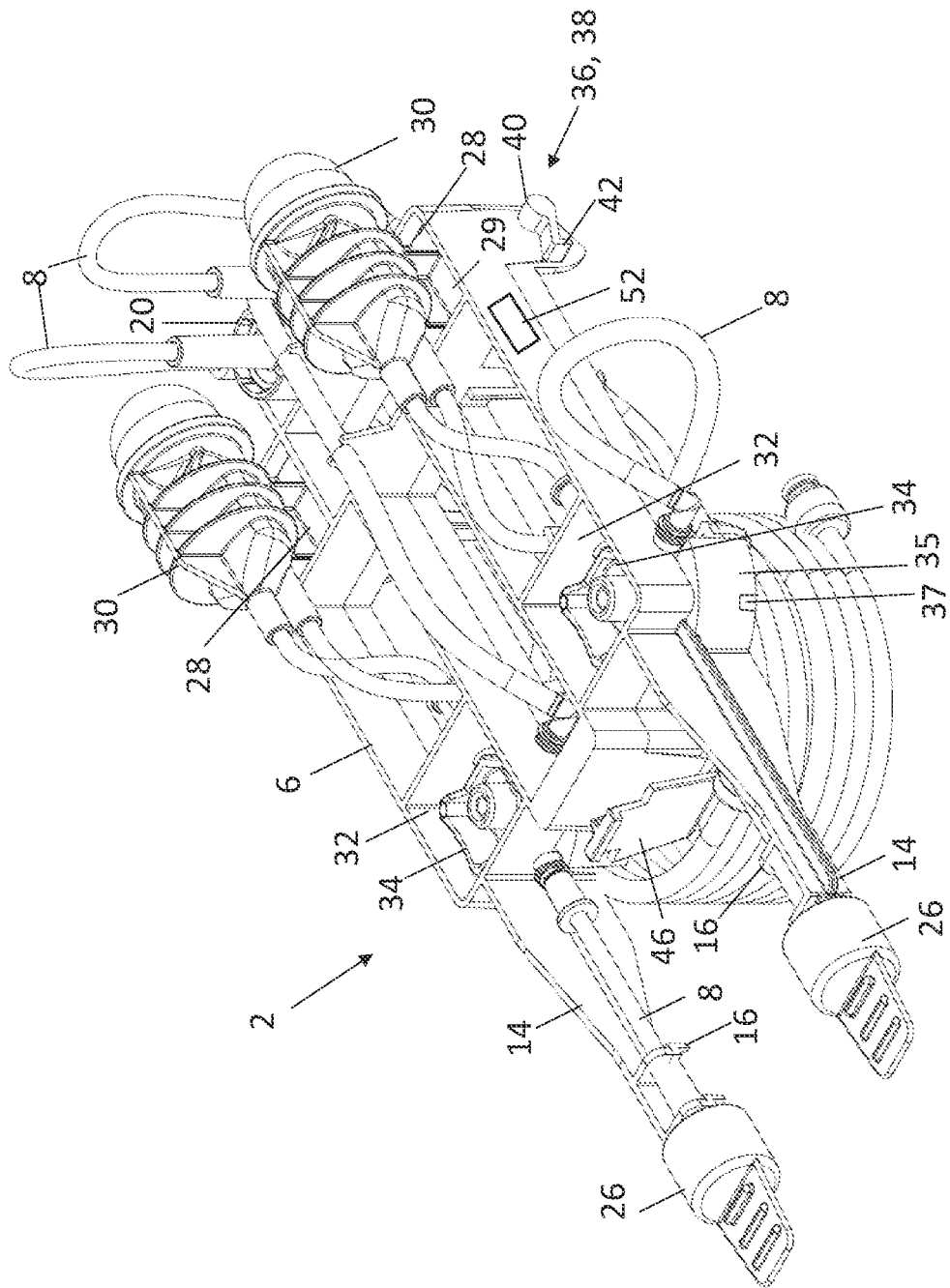
FIG. 4 is a perspective view of the cassette assembly of FIG. 1 with fluid path components attached thereto according to non-limiting embodiments of the present disclosure.
Figure 5:
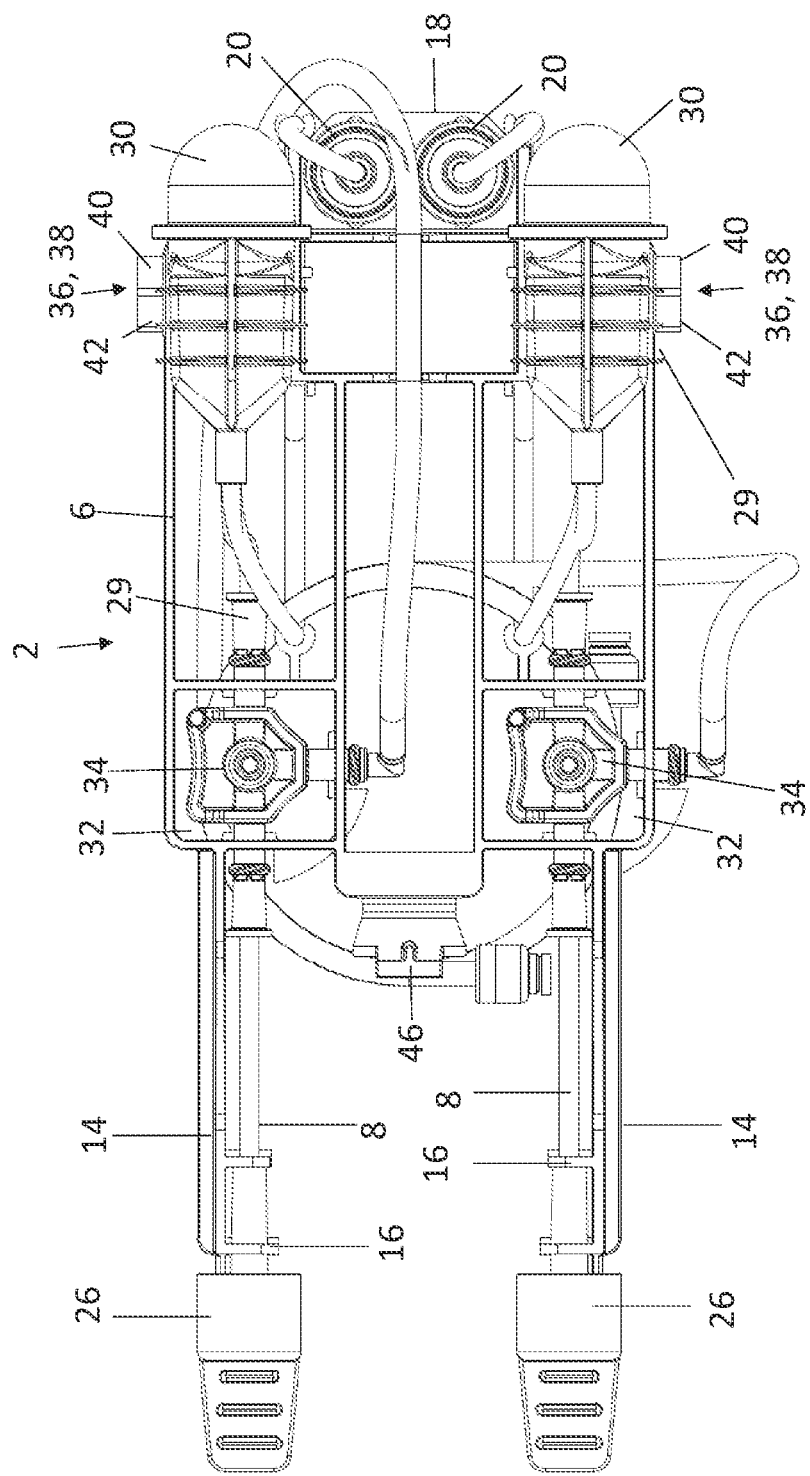
FIG. 5 is a top view of the cassette assembly of FIG. 4.
Figure 19:
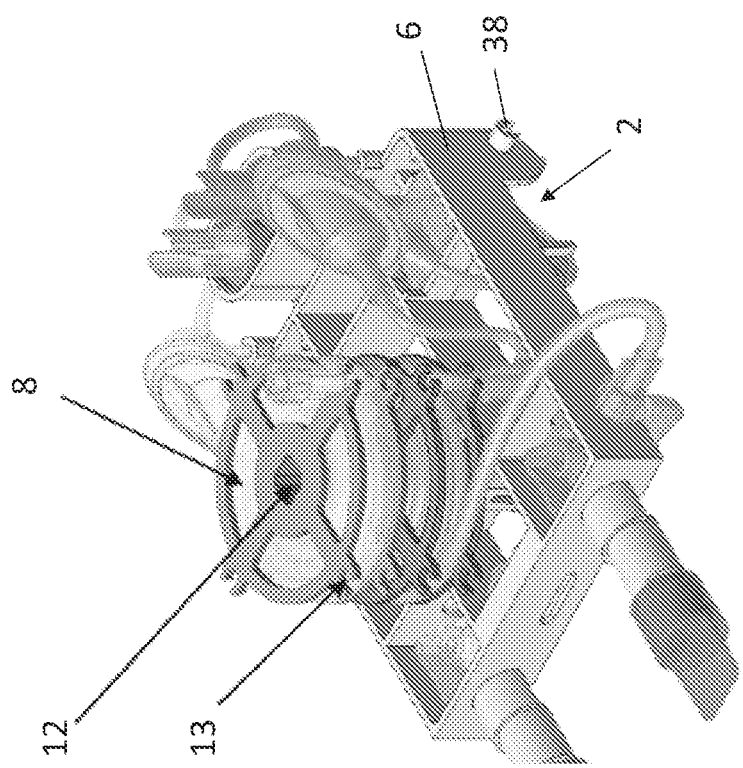
FIG. 19 is a perspective view of a cassette with a spool assembly for holding fluid lines on the cassette according to an embodiment of the present disclosure.
Figure 20:
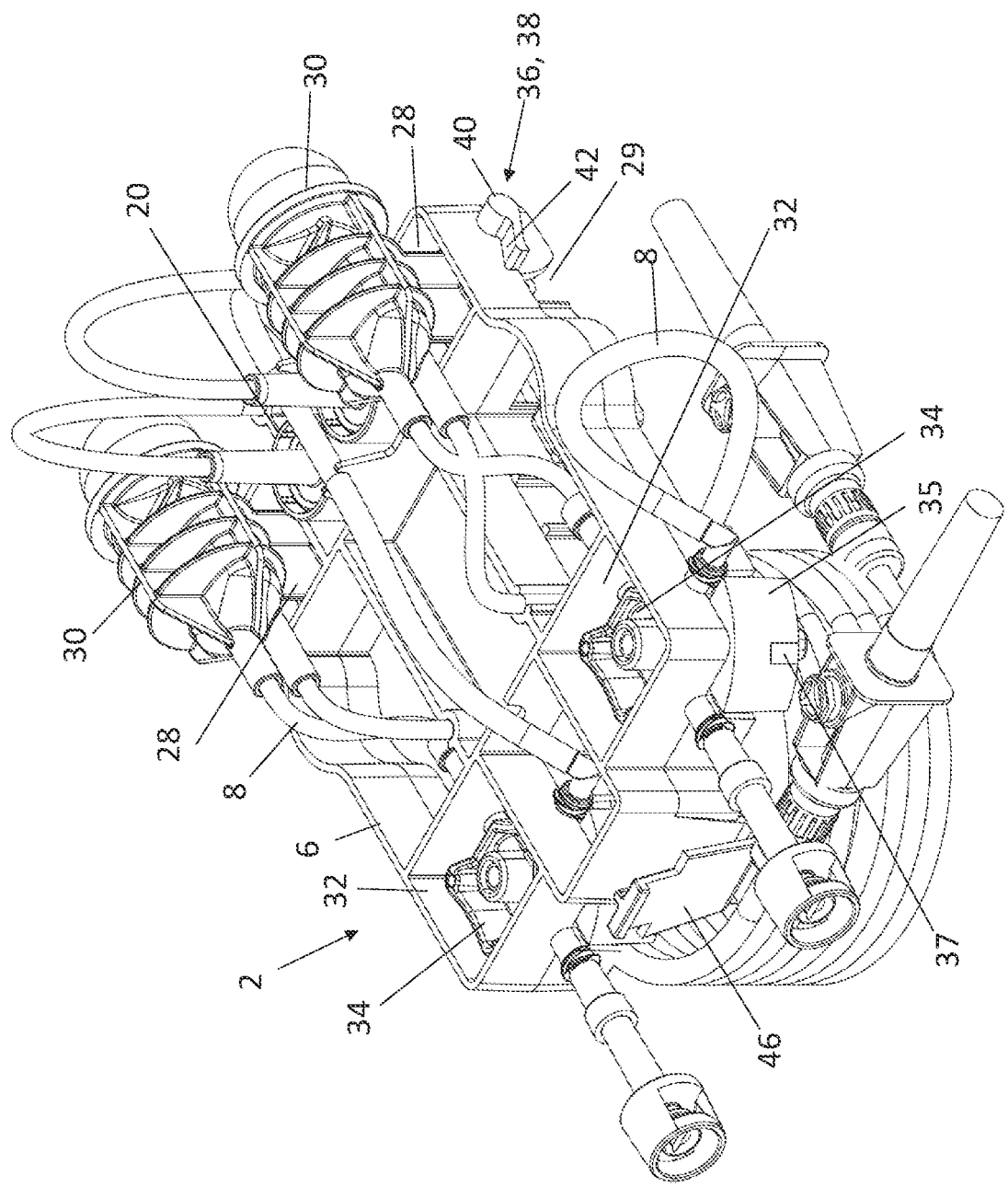
FIG. 20 is a perspective view of a cassette with a spool assembly for holding fluid lines on the cassette according to another embodiment of the present disclosure.

According to non-limiting embodiments and illustrated in FIGS. 4, 19 and 20, one or more spool or reel 12 may be placed on the top, the bottom, or on a side of the cassette 2 to hold various portions of the fluid lines 8 prior to installation and allow the fluid lines 8 to be unreeled. In specific embodiments, the spool 12 could wind from an end or the center of a tubing section. In specific embodiments, the spool 12 could be removable to allow it to be unwound or even installed on the fluid injector 4 to be unwound during setup and rewound after use electromechanically by the fluid injector 4 or by a biasing element, such as a spring, associated with the spool 12. The spool 12 could spin freely or with resistance, such as friction or a click pawl, on the cassette 2. The rotation would allow for easy removal of the fluid lines 8 from the spools 12. The one or more spools 12 could be nestable or stackable such that multiple spools 12 can be used on one cassette 2. In certain embodiments, the spool 12 may include a spring or other biasing member to allow the fluid lines 8 to be retracted, for example by release of a click pawl and spring driven reeling of the fluid lines 8 back onto the spool or reel 12 at the completion of a fluid injection procedure. The spool 12 could have removable end caps or tubing retainers molded into the spool 12 to hold the fluid lines 8 thereon. In one non-limiting embodiment of the present disclosure, the spool 12 may also define retaining grooves 13 that receive and hold the fluid lines 8 when wound on the spool 12.

According to non-limiting embodiments, one or more pocket or well could be molded into the cassette 2 and the fluid lines 8 may be coiled into the cassette 2 prior to setup. The fluid lines 8 could be placed in this pocket in such a way that the fluid lines 8 can be pulled straight out and uncoil itself prior to use with the fluid injector 4. The cassette 2 could also have additional connectors mounted rigidly, such that other fluid line connections are more easily accessed.

According to one embodiment of the present disclosure and illustrated in FIGS. 1-5, the body 6 of the cassette 2 may also include at least one extension member 14 to assist in retaining the distal ends of fluid lines 8 on the cassette 2. For example, the at least one extension member 14 may be configured to hold the distal end of fluid line 8. In one example, the cassette 2 may include a plurality of extension members 14 so that the distal end of each fluid line 8 may be held on separate extension members 14 in a position to be attached to the patient fluid line. The extension members 14 may include retaining tabs 16 that allow the fluid path component, such as fluid lines 8 to be removably secured to the extension members 14. The retaining tab 16 may include grooves defined in the extension members 14 to permit the fluid lines 8 to be press fit into the grooves for retention on the extension members 14. In another embodiment shown in FIG. 20, the cassette 2 may omit extension members 14 and, instead, the fluid lines 8 may extend from a front side of the cassette 2 without support from an extension member or retaining element.

According to various embodiments, the upper and/or lower surfaces of cassette 2 may include a plurality of retention elements to retain various fluid path components in the appropriate position and configuration on the cassette 2, for example, in the correct position and/or orientation for engagement with a corresponding component on the fluid injector or in the proper orientation for a step in an injection procedure. For example, in various embodiments, the retention elements may include one or more catch members to engage a corresponding feature on the fluid path component. The at least one retention element may be configured so that the fluid path component is removably retained by the at least one retention element or the at least one retention element may be configured so that the fluid path component is non-removably retained by the at least one retention element.

Figure 6A:
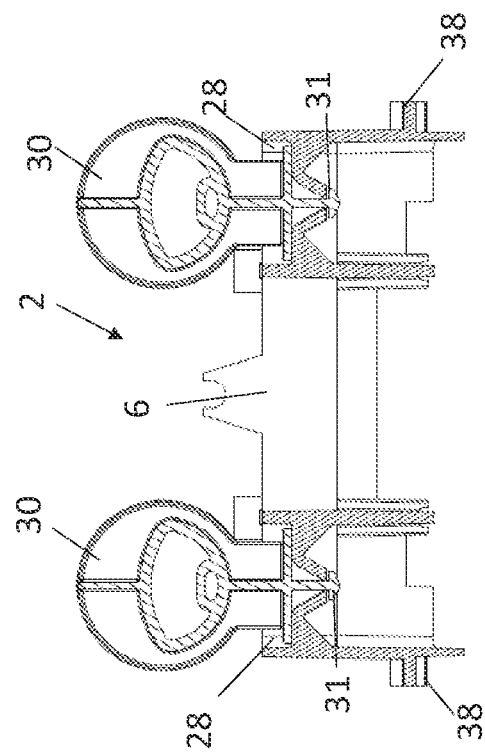

With reference to FIGS. 1-6B, according to various embodiments of the present disclosure, the cassette 2 may define a holder 18 configured to hold one or more removable end caps 20 that are operatively connected to a proximal and/or distal end of one or more the fluid lines 8. The removable end caps 20 may be provided to prevent dust and other microbial contaminants from entering a pre-sterilized fluid path component and contaminating the fluid that moves therethrough. Examples of suitable removable end caps are described, for example, in U.S. Provisional Application No. 63/222,605 or may be commercially available end caps. In certain embodiments, the removable end cap 20 may include a sterilizing element, such as an alcohol swabbing element that maintains sterility of the connector element at the end of the fluid line. The removable end caps 20 may be operatively connected to the fluid lines 8 using a rotational connection, a press-fit or friction-fit connection, or a snap-lock connection. According to various embodiments, the removable end caps 20 may configured to engage one or more flexible locking legs of the corresponding connector element on the fluid line 8, for example as described in PCT Application No. PCT/US2021/018523; or U.S. Pat. No. 11,083,882, the disclosure of which is incorporated herein by this reference. The removable end caps 20 may each have a tab 22 that can be readily gripped by a user to allow removal of the removable end caps 20 from the connector of the fluid line 8 to allow fluid access to the fluid line 8. In one embodiment, the holder 18 may define at least one slot 24 to receive a respective tab 22 of the removable end cap 20 so that the removable end cap 20 and corresponding connector end of the fluid line 8 may be held in a defined position during shipping and installation onto the fluid injector. Alternatively, the holder 18 may be configured to retain another portion of the removable end cap 20. According to various embodiments, the slot 24 may be sized and configured to receive the tab 22 in a friction fit in order to retain the removable end cap 20 in the holder 18 such that the end of the fluid line 8 and connector element are positioned adjacent or near the corresponding feature on the injector, such as a connector element at a distal end of a syringe inserted into the fluid injector 4. After the cassette 2 has been installed on the fluid injector 4, as described herein, and the operator is ready to connect the fluid lines 8 to the connector element at a distal end of a syringe on fluid injector 4, the removable end caps 20 may be pulled from the holder 18 and removed from the fluid lines 8 to allow connection of the fluid lines 8 to the fluid injector 4. In a similar manner to the removable end caps 20, the opposing ends of the fluid lines 8 held on the extension members 14 may also have removable end caps 26 provided thereon to prevent contamination of the fluid lines 8. With reference to FIG. 6B, in accordance with another embodiment of the present disclosure, the tabs 22 of the removable end caps 20 may include a larger tab section that can be press fit into the holder 18 for connection to the cassette 2.

Figure 10:
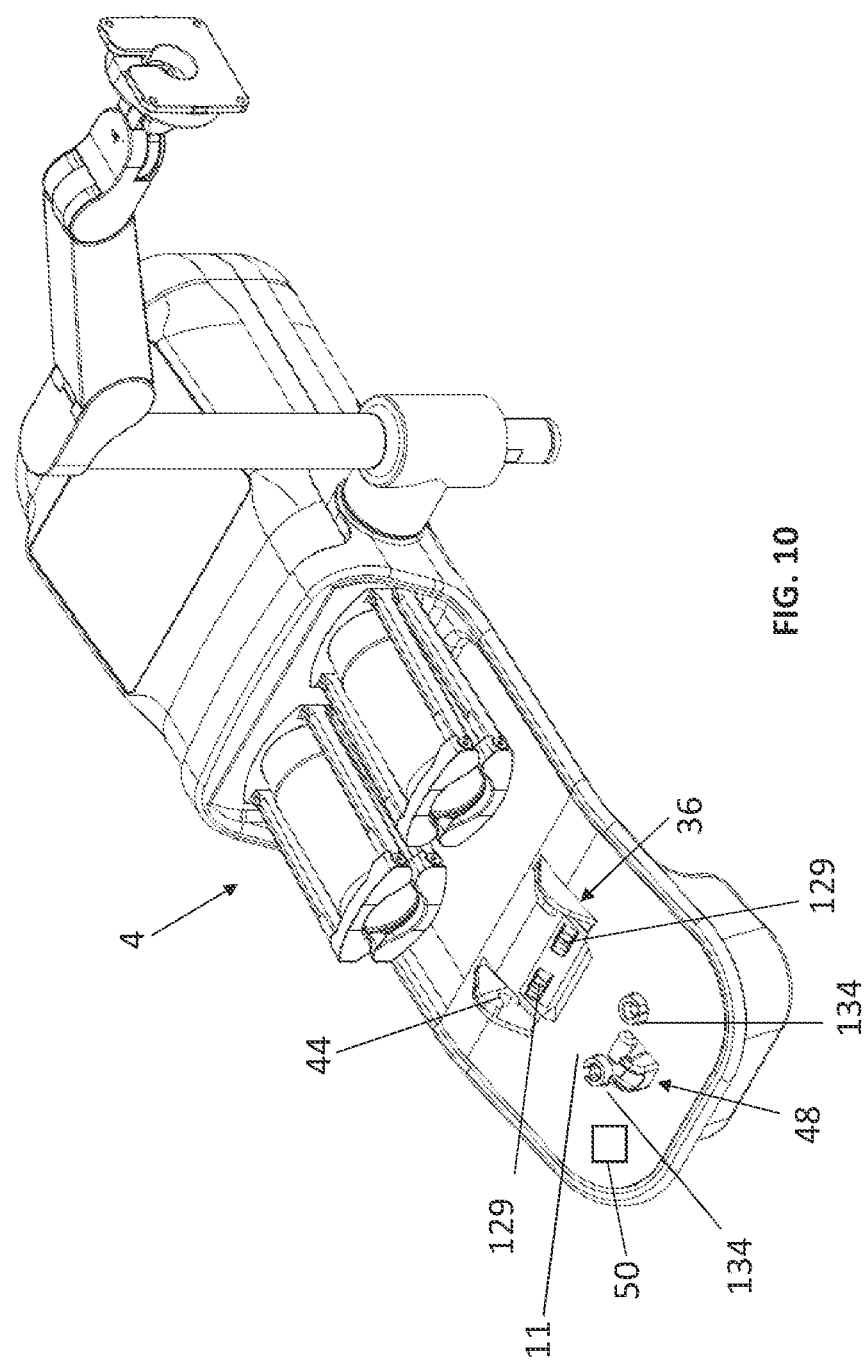
FIG. 10 is a perspective view of a fluid injector including a connection arrangement for receiving the cassette assembly of FIG. 4.
Figure 21:
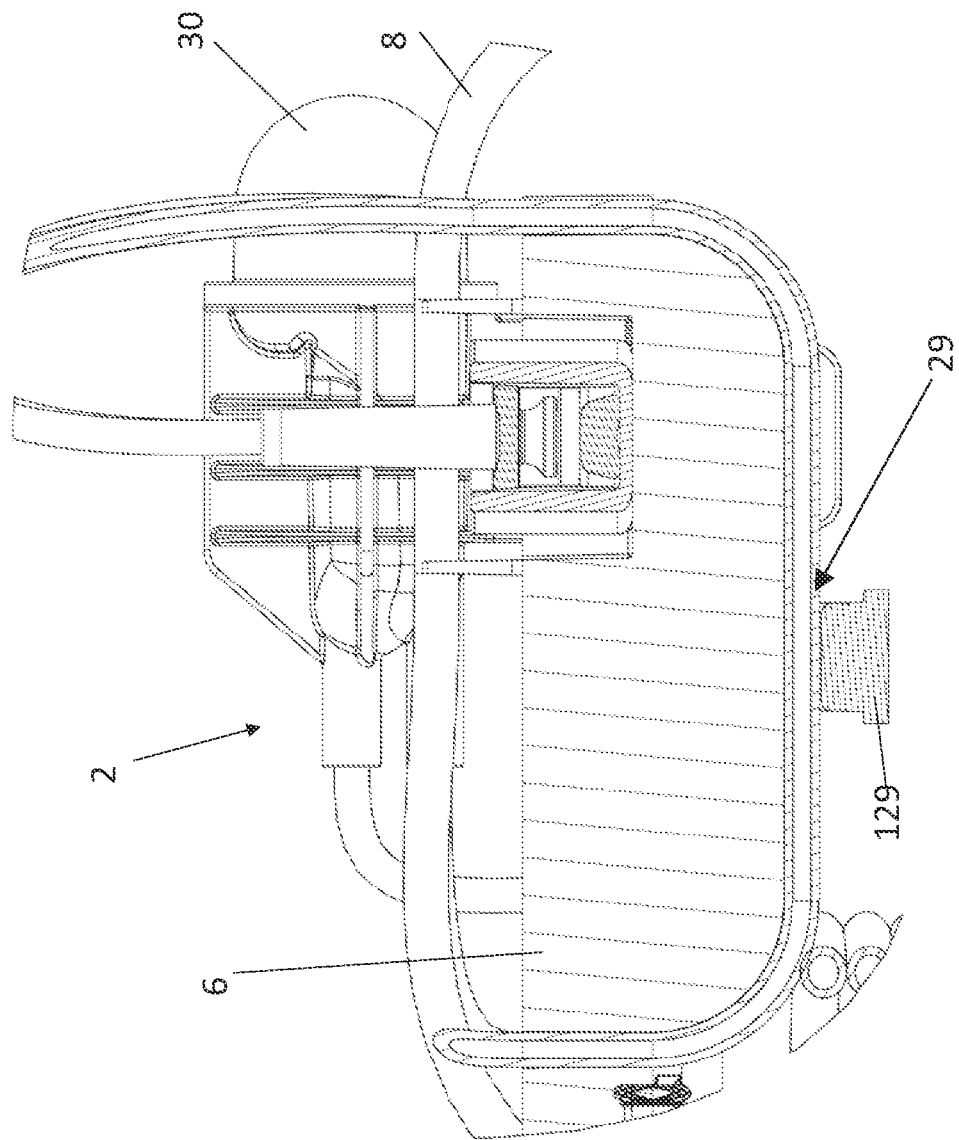
FIG. 21 is a cross-sectional view of the cassette of FIG. 20 showing an air detector operatively interacting with a fluid line.

With reference to FIGS. 1-5, 6A and 6B, and 21 in accordance with various embodiments of the present disclosure, the cassette 2 may also comprise a retention element configured to hold at least one air detection region 29 of the fluid path such that the cassette 2 positions the at least one air detection region 29 to align with one or more air detectors 129 on the receiving surface 11 of fluid injector 4 (see FIGS. 10 and 21). According to various embodiments, the cassette 2 and fluid lines 8 may include two air detection regions 29, a first air detector 29 on the contrast media fluid path and a second air detector 29 on the saline fluid path. According to certain embodiments, each air detection region 29 interacts with a corresponding air detector 129 on the fluid injector 4 so that any air bubble flowing through the fluid path of the at least one air detection region 29 may be detected by an air sensor of the air detector 129. An advantage of the defined scaffolding of the cassette 2 includes that the at least one air detection region 29 is accurately positioned within the corresponding region of the air detector 129 to ensure that any air bubbles that pass through the fluid path in the at least one air detection region 29 are detected by the air detector 129. The air detector 129 is configured to detect one or more air bubbles in the injection fluid during a fluid injection procedure. In response to detecting an air bubble in the injection fluid, the air detector 129 may send a signal to a controller of the fluid injector to indicate that an air bubble has been detected in the fluid line. As will be understood by one of skill in the art, injection of air into the vasculature of a patient may have serious detrimental health effects to the patient. Particularly in angiography procedures, but also in other contrast injection procedures like CT, PET, and MR, it is critical to minimize or eliminate the possibility of injection of a critical volume of air (defined as a minimum volume of air that may cause a detrimental effect if injected into a patient) during a specific procedure. In the present description, the cassette 2 is configured to accurately align the at least one air detection region 29 with one or more corresponding air detectors 129 to eliminate the possibility of operator error or manufacturing defect that may cause misalignment of the at least one air detection region 29 with the air detector 129 and to ensure accurate detection of any air that may pass through the fluid lines 8.

In one embodiment illustrated in FIG. 21, the cassette 2 may be designed and structured to apply a load to the fluid line 8 of the air detection region 29. The geometry and thickness of the cassette 2 may be formed so as to act as a spring and apply a continuous force to the fluid line 8 of the air detection region 29, ensuring contact in the fluid line 8 of the air detection region 29 with the corresponding air detector 129 and account for tolerance issues in manufacturing. For example, as the fluid line 8 of the air detection region 29 is inserted into the cassette 2, the geometry of the cassette 2 and, in particular, a protrusion or retaining element on the cassette 2, may be configured to add pressure against the fluid line 8 to press the air detection region 29 of the fluid line 8 against the air detector 129 to ensure a more accurate reading of the fluid and any air passing through the fluid line 8. By ensuring the cassette 2 is configured to add this pressure against the fluid line 8, any tolerance issues that were created during manufacturing and/or the of the air detection region 29 can be alleviated.

Figure 7A:
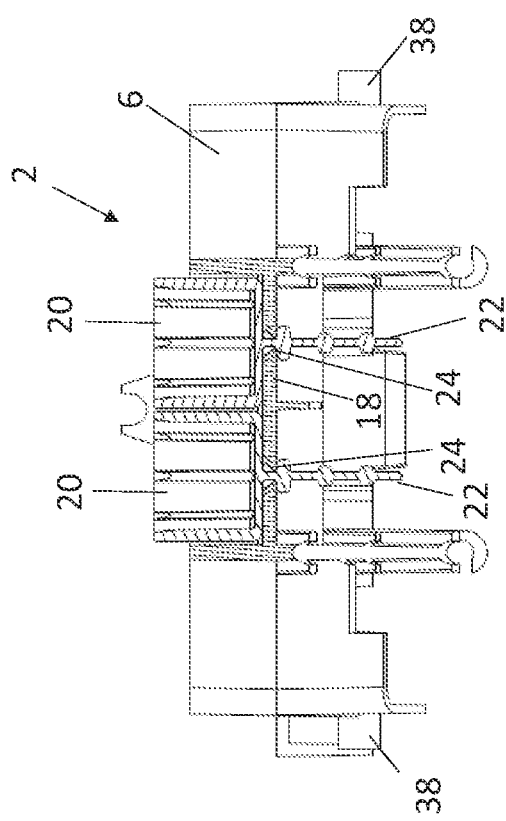
Figure 9:
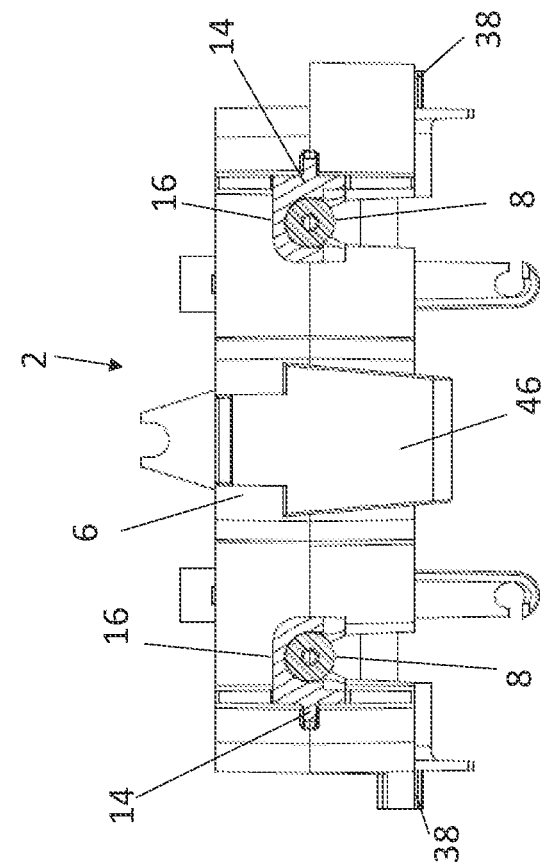
FIG. 9 is a cross-sectional view of the assembly of FIG. 4 showing a fluid line connection to the cassette.
Figure 8:
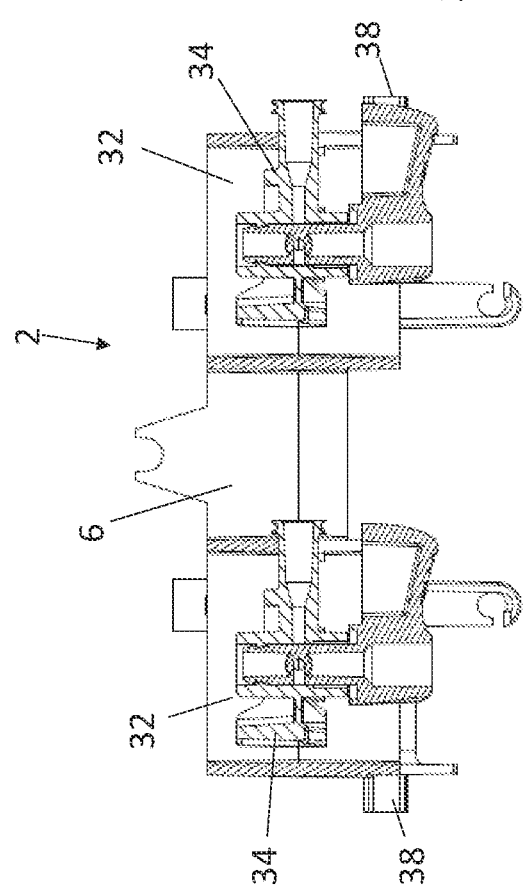
FIG. 8 is a cross-sectional view of the cassette assembly of FIG. 4 showing a stopcock valve connection to the cassette.

In various embodiments, the cassette 2 may define at least one holder 28 configured to receive and retain an air bubble suspension apparatus 30. In one example, the air bubble suspension apparatus 30 may be in fluid connection with a fluid line 8 downstream of the air detection region 29 in order to suspend and delay any air bubbles that may be detected within the fluid passing through the upstream air detection region 29 of the fluid line 8 at least temporarily. For example, the at least one air bubble suspension apparatus 30 may be configured to, at least temporarily, suspend and delay the flow of the one or more detected air bubbles within a bubble suspension region for at least a time sufficient to allow the air detector 129 to signal the controller of the fluid injector 4 that air has been detected and to shut down the fluid injection procedure and stop fluid flow into the patient, for example by moving a shutoff valve, such as a pinch valve or stopcock as described herein, to a closed position. In this manner, even small volumes of air may be detected and the injection procedure shut down before the high fluid flow and system capacitance carries the air bubble into the patient. In one example, the cassette 2 may define two holders 28 each configured to receive and retain a separate air bubble suspension apparatus 30, each of which are in fluid communication with a single fluid line 8 (e.g., the contrast fluid line and the saline fluid line). In one embodiment, the air bubble suspension apparatus 30 may be the in-line air bubble suspension apparatus disclosed in PCT International Patent Application No. PCT/US2021/037623. The air bubble suspension apparatus 30 may be retained in the cassette 2 using latches or snap-fit connectors, among other connection arrangements that permit the air bubble suspension apparatus 30 to be removably attached to the cassette 2. With reference to FIGS. 7A and 7B, in accordance with certain embodiments of the present disclosure, the air bubble suspension apparatus 30 may be held in the cassette 2 using a push tab 31 that is configured to be inserted into an aperture defined in the holder 28. Once the push tab 31 is pushed past the aperture, the push tab 31 is configured to expand outwardly to prevent the push tab 31 from moving back through the aperture of the holder 28.

Figure 14:
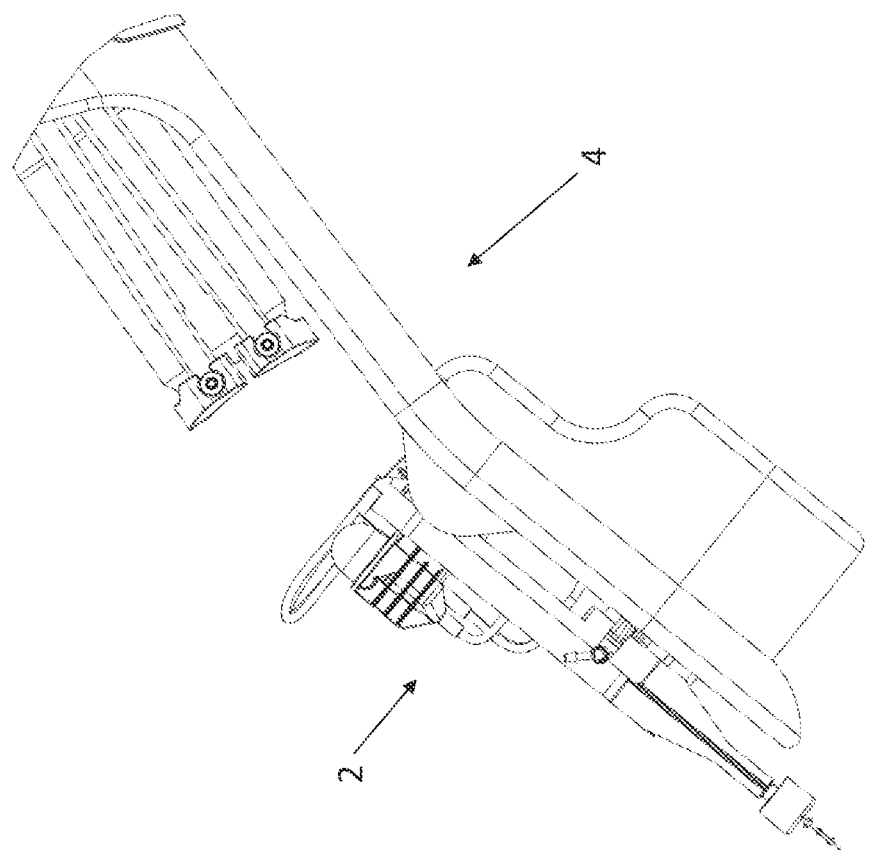
FIG. 14 is a side view of the fluid injector and cassette assembly of FIG. 11 shown in an injection position.
Figure 13:
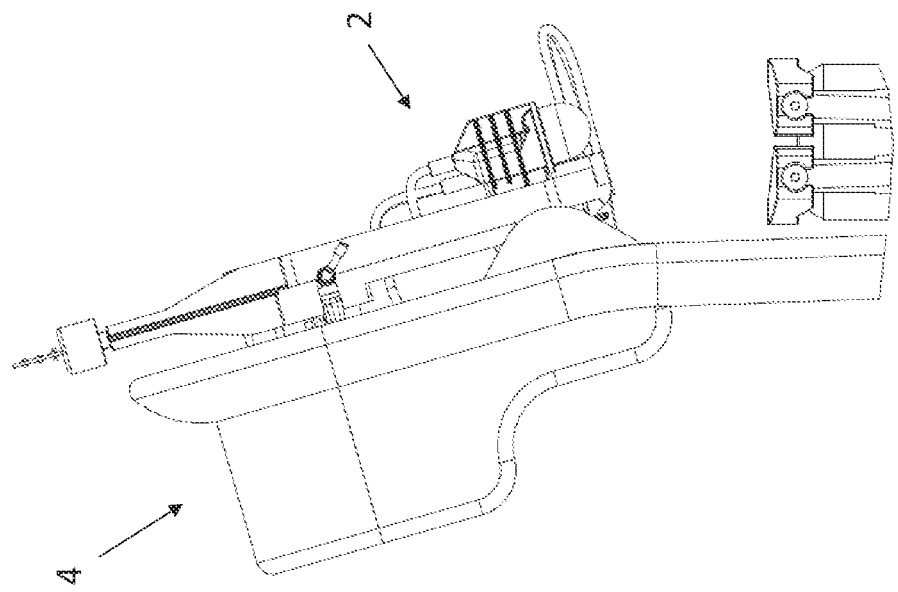
FIG. 13 is a side view of the fluid injector and cassette assembly of FIG. 11 shown in a prime position.

As illustrated in FIGS. 13 and 14, the cassette 2 may be configured to be attached to the fluid injector 4 such that the cassette 2 and fluid injector 4 may be swiveled between an upright priming position (FIG. 13) and a downward facing injection position (FIG. 14). The retention elements associated with the at least one air bubble suspension apparatus 30 of the cassette 2 may align and orient the at least one air bubble suspension apparatus 30 so that it is movable between a first priming position, where substantially all air in the air bubble suspension apparatus 30 may be primed out of the air bubble suspension apparatus 30 and the fluid line before an injection procedure and a second injection position, where the air bubble suspension apparatus 30 is oriented so that it temporarily retains any air bubbles in the fluid path during an injection procedure. Movement of the head of the fluid injector 4 between the upright priming position and the downward angled injection position moves the one or more air bubble suspension apparatus 30 between the priming position to remove air from the air bubble suspension apparatus 30 and the injection position where any air in the injection fluid is retained in the air bubble suspension apparatus 30.

In accordance with one embodiment of the present disclosure, as shown in FIGS. 1-5 and 8, the cassette 2 may also define at least one holder 32 to receive and retain a fluid control valve 34 used to control flow of fluid through the fluid lines 8. In one embodiment, the cassette 2 may define two holder 32 to each receive and retain a fluid control valve 34. In one example, the fluid control valve 34 may be a stopcock valve such as a three-way stopcock. The fluid control valves 34 may be removably held in the holders 32 via a snap-fit connection, friction fit, or any other removable connection arrangement that permits the fluid control valves 34 to be inserted and removed from the holders 32. In one embodiment, the fluid control valves 34, such as a three-way stopcock, are moveable, by the fluid injector 4, between at least three different positions. In a first fluid filling position, the fluid control valves 34 may directed fluid through the fluid lines 8 to provide fluid communication between a bulk fluid source and a syringe held on the fluid injector 4, while preventing fluid communication with the patient fluid line. In a second fluid delivery position, the fluid control valves 34 may be positioned to provide direct fluid communication through the fluid lines 8 from the syringe held in the fluid injector 4 into the patient fluid line and, thus, into the patient, while preventing fluid communication with the bulk fluid source. In a third stopped position, the fluid control valves 34 prevent any fluid communication through the fluid lines 8 between the syringe, the bulk fluid source, and the patient. The cassette may operatively position the stopcock with a corresponding stopcock actuator 134 on the fluid injector 4 so that the stopcock actuators 134 may actuate the corresponding stopcock and move the stopcock between the first, second, and third positions in response to a signal from a controller on the fluid injector 4. For example, when the fluid injection protocol requires filling of the syringe the controller may signal the stopcock actuator 134 to move the stopcock to the first fluid filling position and allow fluid to be withdrawn from a bulk fluid source into a syringe. The controller may then signal the stopcock actuator 134 to move the stopcock to the second fluid delivery position to allow priming of the system, followed by initiation of the fluid injection procedure. The controller may signal the stopcock actuator 134 to move the stopcock to the third stopped position when: a) the fluid injection procedure is temporarily halted to prevent dripping of fluid from the system; b) the fluid injection procedure is over; or c) when the air detector 129 signals the controller that one or more air bubbles have been detected in the fluid flowing through the air detection region 29 of the fluid path. In the latter case, the air detector works in concert with the air bubble suspension apparatus 30, the controller, and the stopcock and stopcock actuator 134 to detect air in the fluid path, temporarily suspend the air in the air bubble suspension apparatus 30, signal the controller that air is detected, allow the controller to signal and actuate the stopcock actuator 134 to move to the third stopped position in a time period that allows fluid flow to be stopped before any air can pass through the air bubble suspension apparatus 30 and downstream to the patient (through the stopcock). The cassette 2 is configured accurately align the stopcock with the stopcock actuator 134 so that the operation may prevent any air from moving through the system into the patient.

According to one embodiment, the fluid control valve 34 may be one or more pinch valves on the fluid injector 4 which may be operatively positioned to interact with one or more fluid lines 8, such as a bulk fluid line and/or a patient fluid line, that is retained in the cassette. In certain embodiments, the pinch valve may be a dual pinch valve designed to control flow through two separate fluid lines, for example between the bulk fluid line and/or a patient fluid line. Suitable pinch valves for incorporation into the fluid injector 4 are described in PCT International Application No. PCT/US2021/029963, such as dual pinch valves described therein. For example, in certain embodiments the dual pinch valve may include a first pinch valve for controlling fluid flow between the bulk fluid source and the syringe and a second pinch valve for controlling fluid flow between the syringe and the patient fluid line. According to specific embodiments, the cassette 2 may be configured to align the various fluid lines 8 with the pinch valve. In specific embodiments, the cassette 2 may be configured to apply a force on the fluid line 8 to bias the fluid line 8 into an engaging interaction (i.e., inserting the fluid line tubing into the pinching region of the pinch valve) when the cassette is operatively engaged with the fluid injector 4.

According to one embodiment, the body 6 of the cassette 2 may include a guard member 35 that covers the at least one fluid control valve 34. The guard member 35 is configured to protect and/or prevent a handle of the at least one fluid control valve 34 from being dislodged during shipping or handling by an operator. In one embodiment, a notch 37 may be provided on the guard member 35 to allow visibility of the handle of the fluid control valve 34 to determine the position of the handle.

According to various embodiments, the cassette 2 includes features that allow for proper locating of the cassette 2 vis-à-vis the receiving surface 11 on the head of the fluid injector 4 and a connection arrangement 36 for ready installation of the cassette 2 on the fluid injector 4 and alignment of the various fluid path components on the cassette 2 with associated features on the fluid injector 4. According to various embodiments, as shown in FIGS. 10-14, the cassette 2 may hingedly engageable to the fluid injector 4 so as to align the fluid lines 8, the bubble suspension apparatuses 30, the air detection regions 29, and the fluid control valves 34 with their corresponding actuators on the fluid injector 4 while locating the ends of the fluid lines 8 adjacent to the corresponding connection feature on the fluid injector 4 and patient fluid lines. Thus, the cassette 2 may increase the efficiency and reduce time between injection procedures while minimizing operator installation error or delay. In certain embodiments, the cassette 2 may be provided as a single packaged disposable unit with all associated disposable fluid path components that may be provided either in sterile packaging or provided as with sterile fluid path components (i.e., the internal portions of the various fluid path components are sterilized and then sealed and packaged). The cassette 2 may be removed from packaging and rapidly engaged with the fluid injector 4 such that all fluid path components on the cassette 2 are ready for the ensuing injection procedure.

Figure 11:
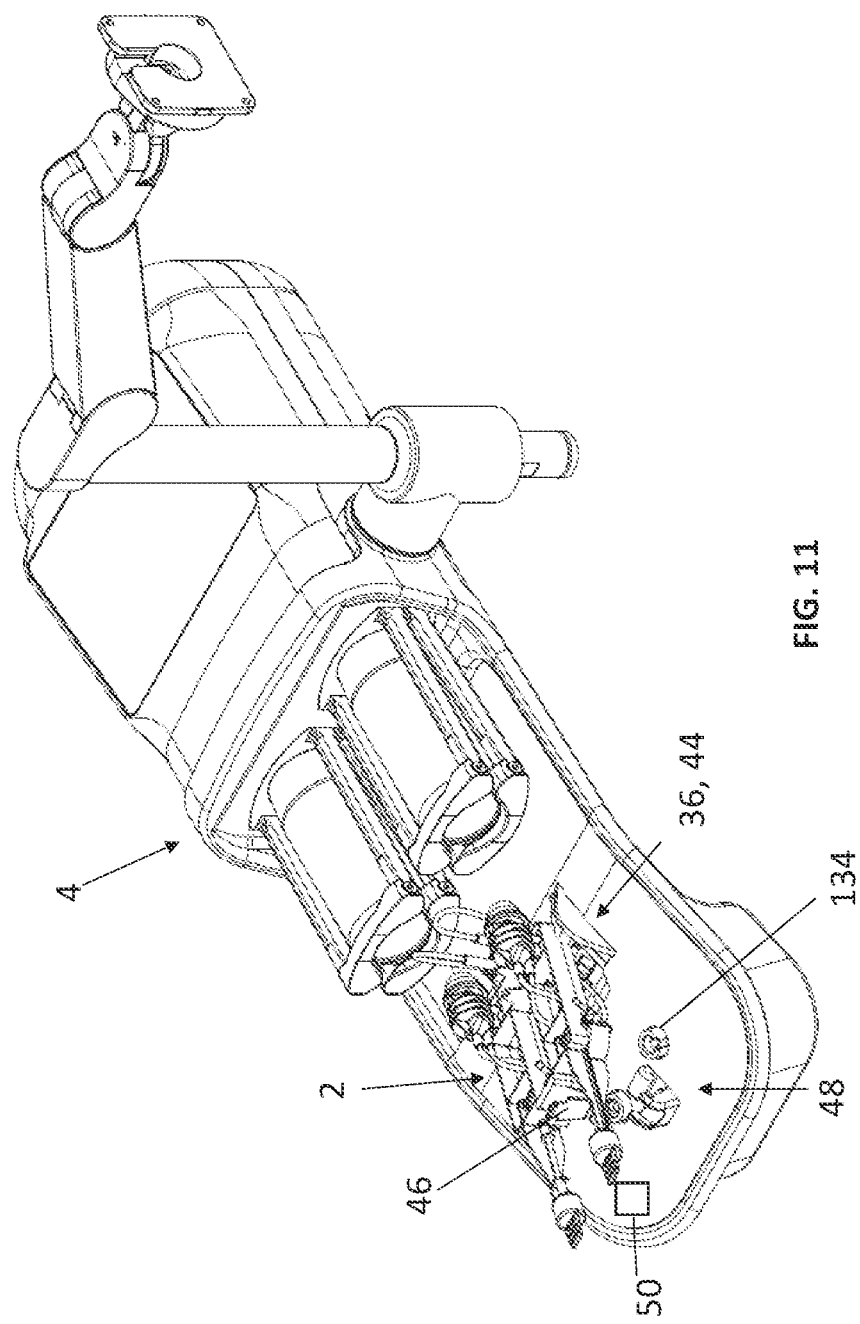
FIG. 11 is a perspective view of the fluid injector of FIG. 10 receiving the cassette assembly of FIG. 4 in a first position.
Figure 12:
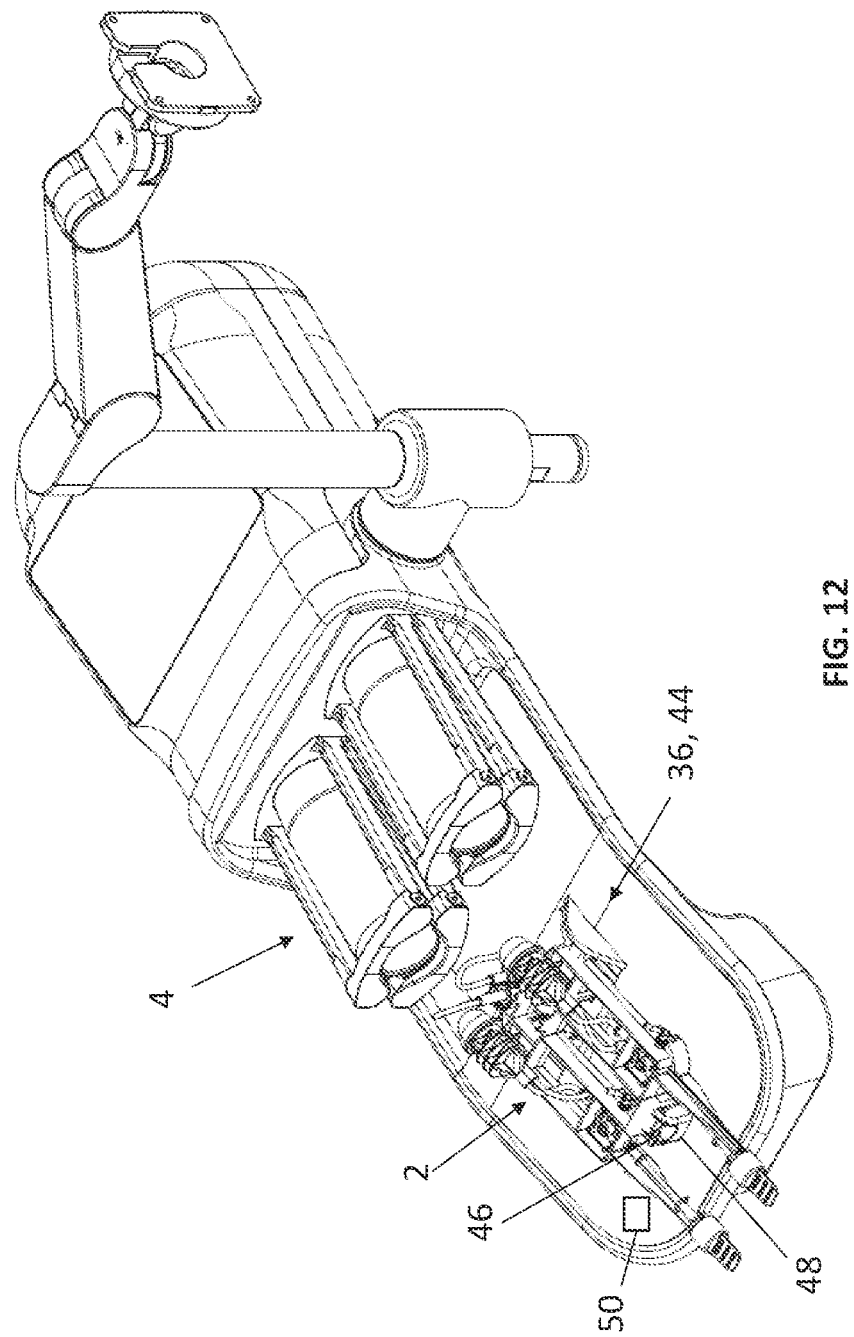
FIG. 12 is a perspective view of the fluid injector of FIG. 10 receiving the cassette assembly of FIG. 4 in a second position.

Various methods for locating, engaging, and latching the cassette 2 to the fluid injector 4 and are shown in FIGS. 10-12, incorporating a fixed pivot point on the fluid injector 4, and secure latching feature for retaining the cassette 2 once positioned and engaged with the receiving surface 11 on the head of fluid injector 4. Once the cassette 2 is attached to and engaged with features of the fluid injector 4, the user may then access the various fluid path components and connect the connector elements, after removal of the associated removable end caps 20, at the distal and proximal ends of the fluid path with the appropriate feature of the fluid injector 4 (e.g., the syringe nozzle, spiking the bulk fluid sources, patient fluid line, etc.) to prepare the system for the fluid injection procedure.

With reference to FIGS. 1-5 and 10-12, in accordance with certain embodiments of the present disclosure, the cassette 2 may include the connection arrangement 36 that includes at least one hinge member 38. In various examples, two hinge members 38 are provided on opposing sides of a proximal end of the cassette 2. Each hinge member 38 may include a rounded member 40 and a latching member 42. In one embodiment, the hinge members 38 are configured to be received within corresponding grooves 44 defined in the cassette receiving surface 11 of the fluid injector 4. In one example, the hinge members 38 may be positioned on the cassette 2 so that the hinge members 38 can only be inserted into the grooves 44 of the receiving surface 11 of fluid injector 4 at a predetermined orientation or an insertion/removal angle relative to the receiving surface 11, thereby eliminating the risk that an operator or user will install the cassette 2 in an undesired position on the fluid injector 4. The grooves 44 may be defined to have a corresponding shape to the hinge members 38. For installation of the cassette 2 onto the fluid injector 4, the rounded members 40 of the hinge members 38 may be first inserted into the grooves 44 on the fluid injector 4. Once the rounded members 40 have been inserted into the grooves 44, the cassette 2 may be rotated downward relative to the fluid injector 4 to bring the cassette 2 towards the fluid injector 4 to cause the latching members 42 of the hinge members 38 to move into the grooves 44. It is also contemplated that the cassette 2 could be press-fit onto the fluid injector 4 instead of a rotational fit.

As shown in FIGS. 10-12, in accordance with various embodiment of the present disclosure, after the hinge members 38 have been inserted into the grooves 44, the cassette 2 may be fully rotated towards the fluid injector 4 for full connection of the cassette 2 to the fluid injector 4. As the cassette 2 is rotated towards the fluid injector 4, a flexible locking tab 46 provided on the distal end of cassette 2 is flexed and pressed into locking engagement with a locking groove 48 defined in the receiving surface 11 of the head of fluid injector 4. The locking tab 46 may snap into engagement with the locking groove 48 to retain the hinge members 38 in the corresponding grooves 44 such that the cassette 2 remains removably engaged with the fluid injector 4. After the cassette 2 has been locked into position on the fluid injector 4, the fluid path components held on the cassette 2 are positioned in a predetermined orientation on the fluid injector 4 for easy connection with corresponding fluid path components on the fluid injector 4 and/or patient fluid line.

For example, in the engaged locked position, the cassette 2 positions the proximal connector ends of the fluid line 8 and the associated removable end cap in close proximity to the distal end of the syringes so that the proximal connector ends may be removed from the removable end cap 20 and the connectors engaged with the syringes to provide fluid communication between the interior of the syringe and the fluid line 8. In one embodiment of the present disclosure, in order to remove the cassette 2 from the fluid injector 4 after use, the locking tab 46 may be flexibly pressed towards the cassette 2 to release from connection with the locking groove 48 on the fluid injector 4, thereby allowing the cassette to be rotated upwards to the insertion/removal angle by rotation of the rounded members 40 of the hinge members 38 within the grooves 44 resulting in disengagement of the fluid path components from the corresponding features of the fluid injector 4 and release of the cassette 2 from the fluid injector 4. The cassette 2 may then be discarded and a new sterile cassette 2 may be installed for a subsequent fluid injection procedure.

Once installed, the cassette 2 may provide a rigid attachment point to the fluid injector 4 to allow for single-handed connection of patient fluid lines 8. Features may also be added to the cassette 2 for storage of the removable end caps 20, as described above. According to certain embodiments, these features could include a removable end cap 20 molded directly into the cassette 2. Additional embodiments may include additional sterile removable end caps for maintaining sterility of the connector end, for example the connector end that attaches to the patient fluid line, after priming of the multi-patient fluid lines 8 and between patient injection procedures. In an alternative embodiment, the cassette 2 may include a sterilizing element, such as an alcohol swabbing feature or feature for accessing a UV light on the fluid injector 4 that allows sterilization of the distal connector end of the fluid line 8 of the cassette 2 between patient injection procedures. The cassette 2 may also serve as a storage location for used removable end caps 20 from setup, which would help maintain a neat workspace and ensure disposal of the removable end caps 20 with the disposable cassette 2. The removable end caps 20 may also be retained on the cassette 2 after removal from the fluid lines 8 to ensure the removable end caps 20 do not fall from the cassette 2.

Removal of the cassette 2 from the fluid injector 4 is simplified, as the cassette 2 provides a one-step, one-handed removal of one or more, for example, all, of multiple fluid path components associated with the cassette 2 when one or a series of multi-patient fluid injections are completed. The cassette 2 can remain attached to the fluid injector and the syringes during this process, for example with the fluid control valve 34 in the third stopped position, minimizing fluid drips between injection procedures in a multi-patient injection set-up or during disassembly steps. The combined syringe and cassette assembly may then be disposed of as a unit. In certain embodiments, the used syringe and cassette assembly may be recycled. Further, maintaining the fluid control valves 34 in the third stopped position, and maintaining the upstream components, such as the syringes and other upstream fluid path components, in the pressurized position may allow for reduction of fluid volume delivery error due to release and uptake of system capacitance (i.e., swelling of system components under injection pressure, uptake of system slack) in between patient injection procedures in a multi-patient injection set-up.

According to some non-limiting embodiments, the cassette 2 may have one or more components that break off once the cassette 2 is removed and renders the cassette 2 and associated fluid path components no longer usable. For example, in certain embodiments, the flexible locking tab 46 or connection arrangement 36 may be configured to break off or deform when disengaged from the fluid injector 4. This avoids accidental reuse of the cassette 2 and associated fluid path components, thus preventing potential cross-contamination and other safety issues associated with multiple uses, beyond those recommended and approved, of the cassette 2 and the fluid path components.

According to some non-limiting embodiments, one or more deformable pieces or shields (not shown) on the cassette 2 could be used to locate components during shipping and installation of the cassette 2 and prevent inadvertent movement of the fluid path components, such as the stopcock handles or engagement feature. For example, during shipment or installation a stopcock engagement feature may be inadvertently moved such that it is no longer in the predetermined position for engagement with the associated stopcock actuator and the shield could prevent access to the engagement feature and minimize the chance of inadvertent movement. These deformable sections could be designed to deflect out of the way when the cassette 2 is installed so that the fluid injector 4 feature, such as an actuator, can interface with the fluid path component, such as the stopcock actuator being able to engage and manipulate the stopcock handle while allowing the controller to identify the specific rotational location of the stopcock so that the controller may accurately move the stopcock between the first, second, and third positions, as described herein.

According to some non-limiting embodiments, portions of the cassette 2 may be illuminated via one or more lights 50 on the fluid injector 4. These lights 50 may include area lighting where the light is cast onto at least a specific portion of or all of the cassette 2. This may also be a directed lighting such as "light piping", where the cassette 2 is designed to transmit light internally through one or more portions of the fluid path or cassette skeletal feature. For certain embodiments, the cassette 2 may be made of transparent or translucent plastic, and the light 50 is close coupled into the cassette 2 on the fluid injector 4. Lighting may be used to indicate to the user that the cassette 2 is properly installed on the injector 4 and/or that the fluid path components are primed and/or that the fluid path components are ready for a fluid injection procedure, and/or which fluid-type (e.g., contrast or saline) is associated with a specific fluid path. Lighting features may also be used to indicate whether the fluid control valves 34 are in the first filling position, the second fluid delivery position, and the third stopped position by use of different colors of light for each position. The cassette 2 may be made of a light transmitting material such that, when the cassette 2 is fully loaded, the light from an emitter is conducted to the transmitter to indicate the cassette 2 is fully loaded.

According to some non-limiting embodiments, the cassette 2 may include one or more identification label 52, such as an RFID, a barcode QR code, or other machine readable identification label, and the identification label 52 may be scanned by the fluid injector 4 or other component of the fluid injector system, such as a controller, a hand-held identification label reader, or computer associated with the fluid injector 4. The identification label 52 may be on one or both of the cassette 2 and the cassette packaging. According to various embodiments, the identification label 52 may be used for a variety of purposes. The identification label 52 may be utilized when setting up the fluid injector 4 to work with the various components and properties of the disposable set (workflow, prime volumes, compliance information, patient count, etc.). According to these embodiments, the cassette 2 may be configured to include different fluid path components depending on the specifics of the injection protocol. An identification label 52 may allow the fluid injector 4 to recognize the features, properties, and components of the specific cassette 2 and associated fluid path components, determine if the cassette 2 is the appropriate cassette 2 for the selected fluid injection procedure, and configure the fluid injection procedure according to the properties and components of the cassette 2. The identification label 52 may further be used prevent reuse of a cassette or use of a cassette beyond an approved life-time and/or may include information of the manufacture of the cassette, such as date of manufacture, usable life-time, etc.

The identification label 52 may also be provided to ensure a compatible, non-counterfeit disposable set is used on the fluid injector 4. The fluid injector 4 may notify the user that the cassette 2 is not a compatible or is not an approved disposable set or is not from an approved manufacturer with appropriate quality control protocols; and may result in one or more errors during a fluid injection procedure, if the fluid path components included on the cassette 2 is used. Upon reading of the identification label 52 the controller may indicate to a user that the cassette 2 is not suitable or approved for the associated injection procedure and may further prevent use of the cassette and associated fluid path components during an injection procedure.

The identification label 52 may also be used for logging usage of the cassette 2 and/or fluid injector 4 for a patient/multiple-patients in a hospital records system. In the event the cassette 2 includes a multi-patient fluid path configuration, the identification label 52 may allow communication and data transfer with a hospital records system or other tracking system to ensure that the cassette 2 and associated components are used according to specifications. The identification label 52 may also be used for alerting a user when the multi-patient disposable set nearing or has reached the maximum usage (maximum number of injections or maximum total use time) or has reached end of shelf-life or expiration and instructing the user on the need for replacement and/or proper disposal of the cassette 2. In another embodiment, an indicator may be provided on the fluid injector 4 to notify an operator when fluid control valves 34 are fully engaged to indicate when the fluid injector 4 is ready for operation.

Figure 16C:
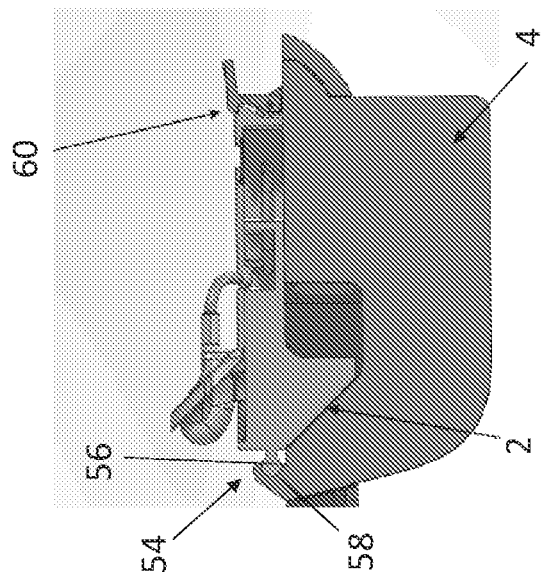
FIGS. 16A-16C are side views of a connection arrangement for a cassette and fluid injector according to another embodiment of the present disclosure.
Figure 16B:
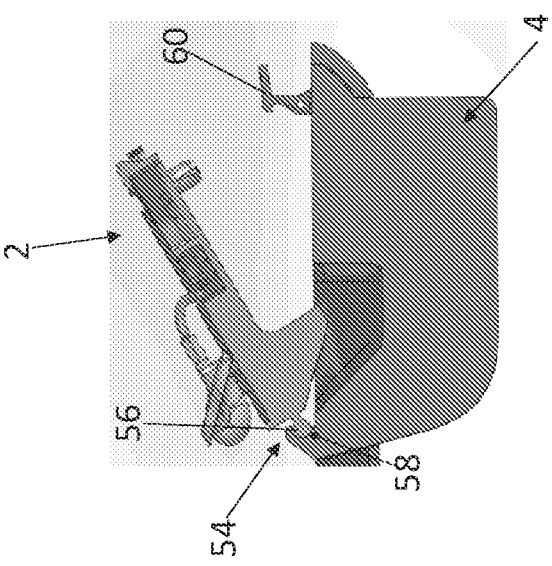
Figure 16A:
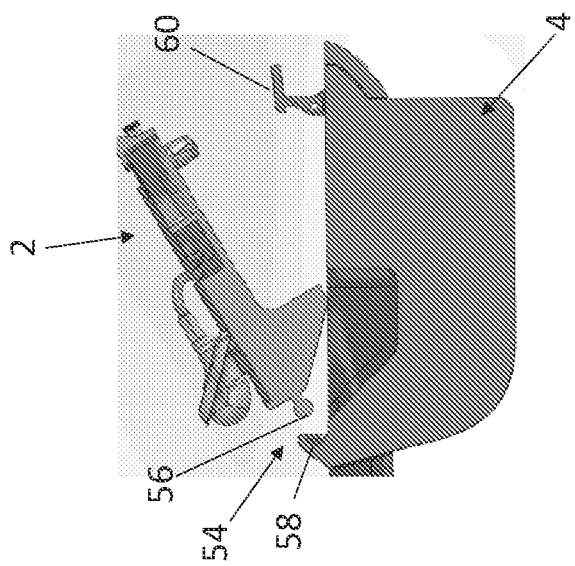

With reference to FIGS. 16A-16C, according to one non-limiting embodiment of the present disclosure, an alternative connection arrangement 54 for connecting a cassette 2 to the fluid injector 4 is shown and described. The connection arrangement 54 may include a locking tab 56 located on the cassette 2 and a locking groove 58 located on the fluid injector 4. In order to connect the cassette 2 to receiving surface 11 of fluid injector 4, the locking tab 56 is inserted into the locking groove 58 on the receiving surface 11 and the cassette 2 may be rotated towards the fluid injector 4. As cassette 2 is rotated towards the fluid injector 4, cassette 2 engages with a latching mechanism 60 to releasably lock cassette 2 to fluid injector 4.

Figure 15:
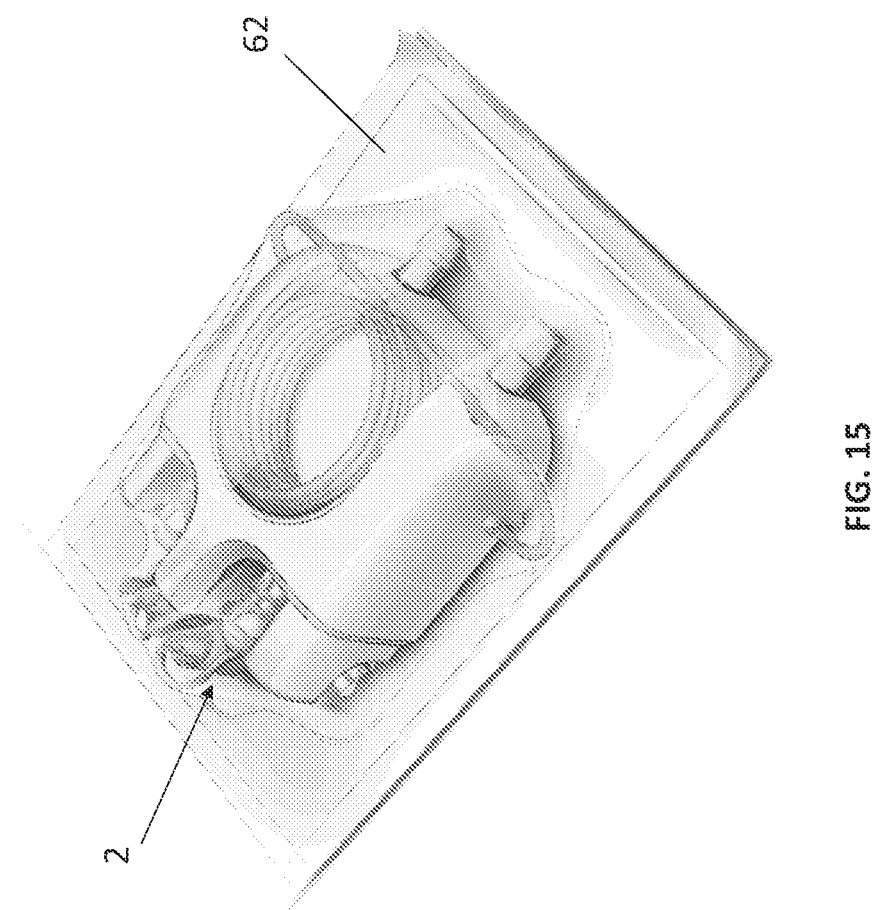
FIG. 15 is a perspective view of a cassette in a packaging according to a non-limiting embodiment of the present disclosure.

With reference to FIG. 15, according to one non-limiting embodiment of the present disclosure, after the fluid path components have been attached to the cassette 2, the entire assembled cassette 2 may be inserted into a press-molded container and/or at least partially covered or wrapped with plastic using a non-permeable or semi-permeable polymeric material or any other known method into a packaging 62. In one example, the patient fluid line may be wound into coils and placed in an associated tubing receptacle on an exterior of the packaging to maintain an organized package. The fluid lines 8 may be banded, individually wrapped, or placed in a sterilized packaging. In addition to using the removable end caps 20, 26 to cover the opposing ends of the fluid lines 8, this packaging method may be used to maintain a sterile fluid path, rather than a completely sterile cassette 2. In another embodiment, a packaging may be formed with the cassette 2 in which two protective coverings are provided on the top and bottom of the cassette 2 to seal the inner components of the cassette 2 from contamination. In one example, the sides of the body 6 of the cassette 2 may form the sides of the packaging.

According to one embodiment of the present disclosure, a method of attaching at least one component to the fluid injector 4 is described. The method may include attaching the at least one component to the cassette 2, the cassette 2 including the body 6 defining at least one aperture for holding the at least one component, and a connecting arrangement or member 36 operatively connected to the body 6. The method may include connecting the cassette 2 to a housing of the fluid injector 4 by operatively connecting the connecting arrangement or member 36 of the cassette 2 to a corresponding connecting arrangement or member 36 on the fluid injector 4. The connection of the cassette 2 to the housing of the fluid injector 4 is configured to position the at least one component at a predetermined location on the housing of the fluid injector 4. The at least one component may be at least one of a stopcock 34, an air bubble suspension apparatus 30, a fluid line 8, and a removable end cap 20 for a fluid line 8. The method may also include evaluating an identifier 52 attached to the cassette 2 to determine whether the cassette 2 has already been used.

It is worthy to note that any reference to "one embodiment" or "an embodiment" means that a particular feature, structure, or characteristic described in connection with the embodiment is included in at least one embodiment. Thus, appearances of the phrases "in one embodiment" or "in an embodiment" in various places throughout the specification are not necessarily all referring to the same embodiment. The particular features, structures, or characteristics may be combined in any suitable manner in one or more embodiments.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the use of any plural and/or singular terms herein, those having skill in the art can translate from the plural to the singular and/or from the singular to the plural as appropriate to the context and/or application. Various singular/plural permutations are not expressly set forth herein for sake of clarity.

The herein described subject matter sometimes illustrates different components contained within, or connected with, other different components. It is to be understood that such depicted architectures are merely exemplary, and that, in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated may be viewed as being "operably connected," and any two components capable of being so associated can also be viewed as being "operably connectable," to each other to achieve the desired functionality. Specific examples of operably connectable include, but are not limited to, physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "operative," "adapted," etc. Those skilled in the art will recognize that "configured to" can generally encompass active-state components, and/or inactive-state components, and/or standby-state components, unless context requires otherwise.

While particular aspects of the subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such recitation to claims containing only one such recitation, even if the same claim includes introductory phrases "one or more" or "at least one" and indefinite articles such as "a" or "an" (e.g., "a" and/or "an" should typically be interpreted to mean "at least one" or "one or more"); this holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

In summary, numerous benefits have been described which result from employing the concepts described herein. The foregoing disclosure has been presented for purposes of illustration and description. It is not intended to be exhaustive or limiting to the precise form disclosed. Modifications or variations are possible in light of the above teachings. It is intended that the claims submitted herewith define the overall scope of the present disclosure.

The invention claimed is:

1. A cassette for holding fluid path components for a fluid injector, the cassette comprising:
a body defining a plurality of retention elements for holding at least one fluid path comprising at least one fluid path component for engagement with the fluid injector, wherein the at least one fluid path component comprises at least one air bubble suspension apparatus retained on the body by at least one of the plurality of retention elements and the at least one air bubble suspension apparatus is fluidly located between a fluid path component comprising at least one air detection region and a fluid path component comprising at least one stopcock; and
at least one connecting member for removably connecting the body to the fluid injector, the at least one connecting member operatively connected to the body,
wherein the at least one connecting member comprises at least one pivotable connecting feature protruding from the body, and
wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body is positioned for operative connection to a corresponding feature of the fluid injector.

2. The cassette of claim 1, further comprising at least one extension member that protrudes from the body, wherein the at least one extension member is configured to hold at least one of the at least one fluid path component of the fluid injector, and
wherein the at least one fluid path component is further selected from at least one of at least one second stopcock, at least one second air bubble suspension apparatus, one or more fluid lines, at least one fluid path components comprising a second air detection region, and at least one removable end cap for the one or more fluid lines.

3. The cassette of claim 2, wherein the at least one extension member includes a retaining tab for holding the fluid path component on the at least one extension member.

4. The cassette of claim 1, wherein the at least one stopcock comprises a first fluid filling position providing fluid communication between a bulk fluid container and a syringe engaged to the fluid injector, a second fluid delivery position providing fluid communication between the syringe and a patient tubing set, and a third stopped position blocking fluid communication between the syringe, the bulk fluid container, and the patient tubing set, and
wherein at least one of the plurality of retention elements retains the at least one stopcock in a position configured to engage at least one stopcock actuator of the fluid injector when the cassette is in the second latched position.

5. The cassette of claim 4, wherein the body further comprises a shield member that prevents a user from accessing the at least one stopcock held in the body.

6. The cassette of claim 1,
wherein the at least one of the plurality of retention elements retains the at least one air bubble suspension apparatus in a position to be movable between a first priming position and a second injection position with movement of a head of the fluid injector between an upright priming position and a downward angled injection position.

7. The cassette of claim 6, wherein the at least one air bubble suspension apparatus is configured to prime substantially all air bubbles out of the at least one air bubble suspension apparatus when primed in the first priming position; and configured to at least temporarily suspend any air bubble detected in an injection fluid during a fluid injection procedure when in the second injection position.

8. The cassette of claim 4, wherein the at least one fluid path component comprises at least one fluid path components comprising an air detection region,
wherein at least one of the plurality of retention elements retains the at least one fluid path components comprising an air detection region in a position to operatively engage an air detector on a receiving surface of the fluid injector.

9. The cassette of claim 8, wherein the air detector is configured to detect an air bubble in an injection fluid during a fluid injection procedure, and in response to detecting the air bubble in the injection fluid, send a signal to a controller of the fluid injector to cause the at least one stopcock actuator to move the at least one stopcock from the second fluid delivery position, and the third stopped position.

10. The cassette of claim 2, wherein the cassette comprises two stopcocks, two air bubble suspension apparatuses, a plurality of fluid lines, two fluid path components each comprising an air detection region, and a plurality of removable end caps for the plurality of fluid lines.

11. The cassette of claim 1, wherein the at least one connecting member further comprises a flexible locking tab that is configured to be received in a corresponding locking groove on the fluid injector for removably attaching the body to the fluid injector.

12. The cassette of claim 1, wherein the at least one pivotable connecting feature of the at least one connecting member comprises at least one hinge member configured to removably connect with at least one groove on the corresponding connecting feature receiver on a receiving surface of the fluid injector.

13. The cassette of claim 1, further comprising an identification label positioned on the body, wherein the identification label is configured to provide information regarding the cassette including at least one of date of assembly, number of uses of the cassette, and location of the cassette.

14. A fluid injector, comprising:
a housing;
at least one syringe removably held in the housing; and
a cassette for holding fluid path components for the fluid injector, the cassette comprising:
  a body defining a plurality of retention elements for holding at least one fluid path comprising at least one fluid path component for engagement with the fluid injector, wherein the at least one fluid path component comprises at least one air bubble suspension apparatus retained on the body by at least one of the plurality of retention elements and the at least one air bubble suspension apparatus is fluidly located between a fluid path component comprising at least one air detection region and a fluid path component comprising at least one stopcock; and
  at least one connecting member for removably connecting the body to the fluid injector, the connecting member operatively connected to the body,
  wherein the at least one connecting member comprises at least one pivotable connecting feature protruding from the body, and
  wherein each of the at least one pivotable connecting feature is configured for removably connecting to a corresponding connecting feature receiver on the fluid injector such that the body is pivotally movable relative to the fluid injector between a first, unlatched position and a second, latched position in which the at least one fluid path component on the body is positioned for operative connection to a corresponding feature of the fluid injector.

15. The fluid injector of claim 14, wherein the at least one fluid path component is further selected from at least one of at least one second stopcock, at least one second air bubble suspension apparatus, one or more fluid lines, at least one fluid path components comprising a second air detection region, and at least one removable end cap for the one or more fluid lines.

16. The fluid injector of claim 15, further comprising at least one stopcock actuator,
wherein the at least one stopcock comprises a first fluid filling position providing fluid communication between at least one bulk fluid container and the at least one syringe engaged to the fluid injector, a second fluid delivery position providing fluid communication between the at least one syringe and a patient tubing set, and a third stopped position blocking fluid communication between the at least one syringe, the at least one bulk fluid container, and the patient tubing set, and
wherein the at least one stopcock is retained by at least one of the plurality of retention elements in a position configured to engage the at least one stopcock actuator of the fluid injector when the cassette is in the second latched position.

17. The fluid injector of claim 16, wherein the at least one stopcock actuator actuates the at least one stopcock between the first fluid filling position, the second fluid delivery position, and the third stopped position is response to a signal from a controller of the fluid injector.

18. The fluid injector of claim 15, further comprising a head movable between an upright priming position and a downward angled injection position,
wherein the at least one air bubble suspension apparatus is retained by at least one of the plurality of retention elements in a position to be movable between a first priming position and a second injection position with movement of the head of the fluid injector between the upright priming position and the downward angled injection position.

19. The fluid injector of claim 15, further comprising at least one air detector on a receiving surface of the fluid injector,
wherein the at least one path fluid component comprises at least one fluid path components comprising an air detection region retained by at least one of the plurality of retention elements in a position to operatively engage the at least one air detector.

20. The fluid injector of claim 19, wherein the at least one air detector is configured to detect an air bubble in an injection fluid during a fluid injection procedure, and in response to detecting the air bubble in the injection fluid, send a signal to a controller of the fluid injector to cause the at least one stopcock actuator to move the at least one stopcock from the second fluid delivery position, and the third stopped position.

21. The fluid injector of claim 14, further comprising at least one locking groove, wherein the at least one connecting member further comprises a flexible locking tab configured to be received in the corresponding at least one locking groove for removably attaching the body to the fluid injector.

22. The fluid injector of claim 14, further comprising at least one groove on the corresponding connecting feature receiver on a receiving surface of the fluid injector,
wherein the at least one pivotable connecting feature of the at least one connecting member comprises at least one hinge member configured to removably connect with the at least one groove.

23. A method of attaching at least one fluid path to a fluid injector, the method comprising:
removably connecting a cassette to a housing of the fluid injector by operatively connecting at least one connecting member of the cassette to a corresponding connecting feature receiver on a receiving surface of the fluid injector,
wherein the cassette comprises:
  a body comprising a plurality of retention elements for holding the at least one fluid path comprising at least one fluid path component for engagement with the fluid injector, wherein the at least one fluid path component comprises at least one air bubble suspension apparatus retained on the body by at least one of the plurality of retention elements and the at least one air bubble suspension apparatus is fluidly located between a fluid path component comprising at least one air detection region and a fluid path component comprising at least one stopcock; and the at least one connecting member having at least one pivotable connecting feature protruding from the body, wherein the connection of the cassette to the housing of the fluid injector positions the at least one fluid path component at a predetermined location on the housing of the fluid injector.

24. The method of claim 23, further comprising evaluating an identification label attached to the cassette to determine whether the cassette has been previously used.

* * * * *

UNITED STATES PATENT AND TRADEMARK OFFICE
CERTIFICATE OF CORRECTION

PATENT NO. : 12,023,464 B2
APPLICATION NO. : 18/254586
DATED : July 2, 2024
INVENTOR(S) : Naples et al.

Page 1 of 1

It is certified that error appears in the above-identified patent and that said Letters Patent is hereby corrected as shown below:

In the Specification

In Column 2, Line 53, delete "position is" and insert -- position in --, therefor.
In Column 4, Line 15, delete "position is" and insert -- position in --, therefor.
In Column 6, Line 16, delete "position is" and insert -- position in --, therefor.
In Column 8, Line 12, delete "position is" and insert -- position in --, therefor.
In Column 11, Line 44, delete "alone" and insert -- along --, therefor.
In Column 12, Line 40, delete "embodiment" and insert -- embodiment of --, therefor.
In Column 16, Line 24, delete "and/or the of the" and insert -- of the --, therefor.
In Column 18, Line 12, delete "configured" and insert -- configured to --, therefor.
In Column 20, Line 3, delete "cap" and insert -- cap 20 --, therefor.
In Column 20, Line 28, delete "caps" and insert -- caps 20 --, therefor.
In Column 22, Line 12, delete "used" and insert -- used to --, therefor.

In the Claims

In Column 28, Line 7, in Claim 17, delete "position is" and insert -- position in --, therefor.

Signed and Sealed this
Second Day of September, 2025

Coke Morgan Stewart
*Acting Director of the United States Patent and Trademark Office*